US011773450B2

(12) United States Patent
Yip et al.

(10) Patent No.: US 11,773,450 B2
(45) Date of Patent: Oct. 3, 2023

(54) METHYLATION-BASED FALSE POSITIVE DUPLICATE MARKING REDUCTION

(71) Applicant: GRAIL, Inc., Menlo Park, CA (US)

(72) Inventors: Alexander S. Yip, Menlo Park, CA (US); Samuel S. Gross, Sunnyvale, CA (US); Seyedmehdi Shojaee, San Francisco, CA (US)

(73) Assignee: GRAIL, LLC, Menlo Park, CA (US)

( * ) Notice: Subject to any disclaimer, the term of this patent is extended or adjusted under 35 U.S.C. 154(b) by 810 days.

(21) Appl. No.: 16/839,469

(22) Filed: Apr. 3, 2020

(65) Prior Publication Data

US 2020/0340063 A1   Oct. 29, 2020

Related U.S. Application Data

(60) Provisional application No. 62/828,899, filed on Apr. 3, 2019.

(51) Int. Cl.
| | | |
|---|---|---|
| *G01N 33/48* | (2006.01) | |
| *C12Q 1/6886* | (2018.01) | |
| *G16B 5/20* | (2019.01) | |
| *G16B 30/10* | (2019.01) | |
| *G16B 40/00* | (2019.01) | |
| *G16B 20/00* | (2019.01) | |

(52) U.S. Cl.
CPC ............. *C12Q 1/6886* (2013.01); *G16B 5/20* (2019.02); *G16B 20/00* (2019.02); *G16B 30/10* (2019.02); *G16B 40/00* (2019.02); *C12Q 2600/154* (2013.01)

(58) Field of Classification Search
None
See application file for complete search history.

(56) References Cited

U.S. PATENT DOCUMENTS

| | | |
|---|---|---|
| 2016/0017419 A1 | 1/2016 | Chiu et al. |
| 2016/0017430 A1 | 1/2016 | Badosa |
| 2016/0210403 A1 | 7/2016 | Zhang et al. |
| 2016/0340740 A1 | 11/2016 | Zhang |
| 2017/0121767 A1 | 5/2017 | Dor et al. |
| 2017/0175205 A1 | 6/2017 | Toung et al. |
| 2018/0341745 A1 | 11/2018 | Zhang et al. |
| 2019/0287652 A1 | 9/2019 | Gross et al. |

FOREIGN PATENT DOCUMENTS

| | | |
|---|---|---|
| WO | WO 2014/043763 A1 | 3/2014 |
| WO | WO 2015/159292 A2 | 10/2015 |
| WO | WO 2016/115530 A1 | 7/2016 |
| WO | WO 2019/195268 A2 | 10/2019 |

OTHER PUBLICATIONS

Sontag, Laura B., Matthew C. Lorincz, and E. Georg Luebeck. "Dynamics, stability and inheritance of somatic DNA methylation imprints." Journal of theoretical biology 242.4 (2006): 890-899.*
Tsai, Albert G., et al. "Heterogeneity and randomness of DNA methylation patterns in human embryonic stem cells." DNA and cell biology 31.6 (2012): 893-907.*
Zackay, Arie, and Christine Steinhoff. "MethVisual-visualization and exploratory statistical analysis of DNA methylation profiles from bisulfite sequencing." BMC research notes 3.1 (2010): 1-8.*
"IHEC—International Human Epigenome Consortium,", Date Unknown, four pages, [Online] [Retrieved on Apr. 3, 20201 Retrieved from the Internet <URL: http://ihec-epigenomes.org/>.
Grail, Inc., "The Circulating Cell-free Genome Atlas Study (CCGA)," ClinicalTrials.gov Identifier: NCT02889978, Feb. 11, 2019, six pages, [Online] [Retrieved on Apr. 3, 2020] Retrieved from the Internet <URL: https://www.clinicaltrials.gov/ct2/show/NCT02889978>.
Guo, S. et al., "Identification of methylation haplotype blocks aids in deconvolution of heterogeneous tissue samples and tumor tissue-of-origin mapping from plasma DNA," Nature Genetics, vol. 49, No. 4, Apr. 2017, pp. 635-644.
Kang, S. et al., "CancerLocator: non-invasive cancer diagnosis and tissue-of-origin prediction using methylation profiles of cell-free DNA," Genome Biology, vol. 18, No. 53, 2017, pp. 1191-1195.
Milani, L. et al., "DNA methylation for subtype classification and prediction of treatment outcome in patients with childhood acute lymphoblastic leukemia," Blood, vol. 115, No. 6, Feb. 11, 2010, pp. 1214-1225.
PCT International Search Report and Opinion, PCT Application No. PCT/US2019/068060, dated Apr. 17, 2020, 19 pages.
PCT International Search Report and Opinion, PCT Application No. PCT/US2019/068014, dated Apr. 17, 2020, 17 pages.
PCT International Search Report and Written Opinion, PCT Application No. PCT/US2019/022122, dated Aug. 23, 2019, 25 pages.
PCT Invitation to Pay, PCT Application No. PCT/US2019/022122, Jul. 1, 2019, 23 pages.
Shen, S. Y. et al., "Sensitive tumour detection and classification using plasma cell-free DNA methylomes," Nature, vol. 563, Nov. 22, 2018, pp. 579-583.
Xu, R. et al., "Circulating tumour DNA methylation markers for diagnosis and prognosis of hepatocellular carcinoma," Nature Materials, Oct. 9, 2017, pp. 1-8.

* cited by examiner

*Primary Examiner* — Anna Skibinsky
(74) *Attorney, Agent, or Firm* — Fenwick & West LLP

(57) ABSTRACT

An analytics system marks duplicate fragments from an initial set of fragments from a subject. The analytics system generates a sample state vector for each fragment. Each sample state vector comprises a sample genomic location within a reference genome and a plurality of methylation states for a plurality of CpG sites in the fragment, the methylation states determined to be one of methylated, unmethylated, variant, and ambiguous. The analytics system identifies two fragments with methylation state vectors as being derived from a matching reference location, e.g., sharing a common plurality of CpG sites. The analytics system calculates a modified Hamming distance based on methylation states in the first sample state vector and methylation states in the second sample state vector. Based on the modified Hamming distance, the analytics system marks the first fragment and the second fragment as either duplicate fragments or non-duplicate fragments.

21 Claims, 12 Drawing Sheets

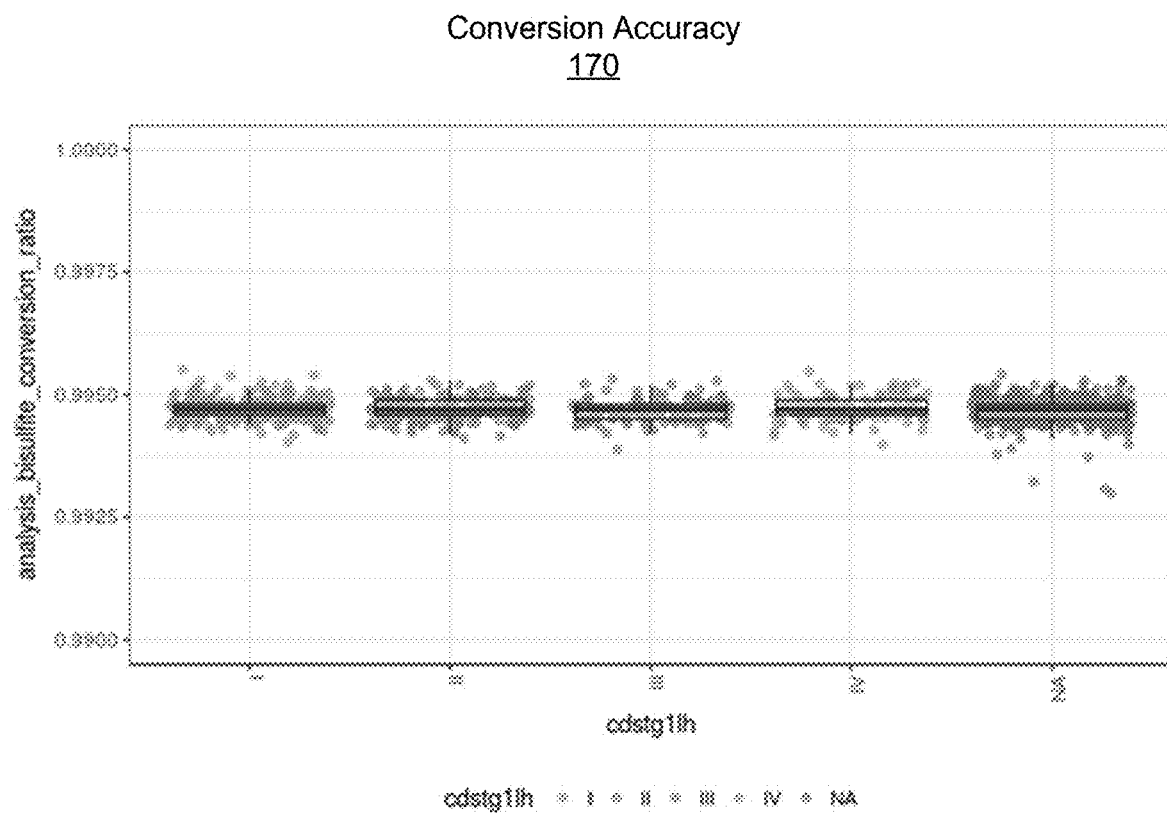
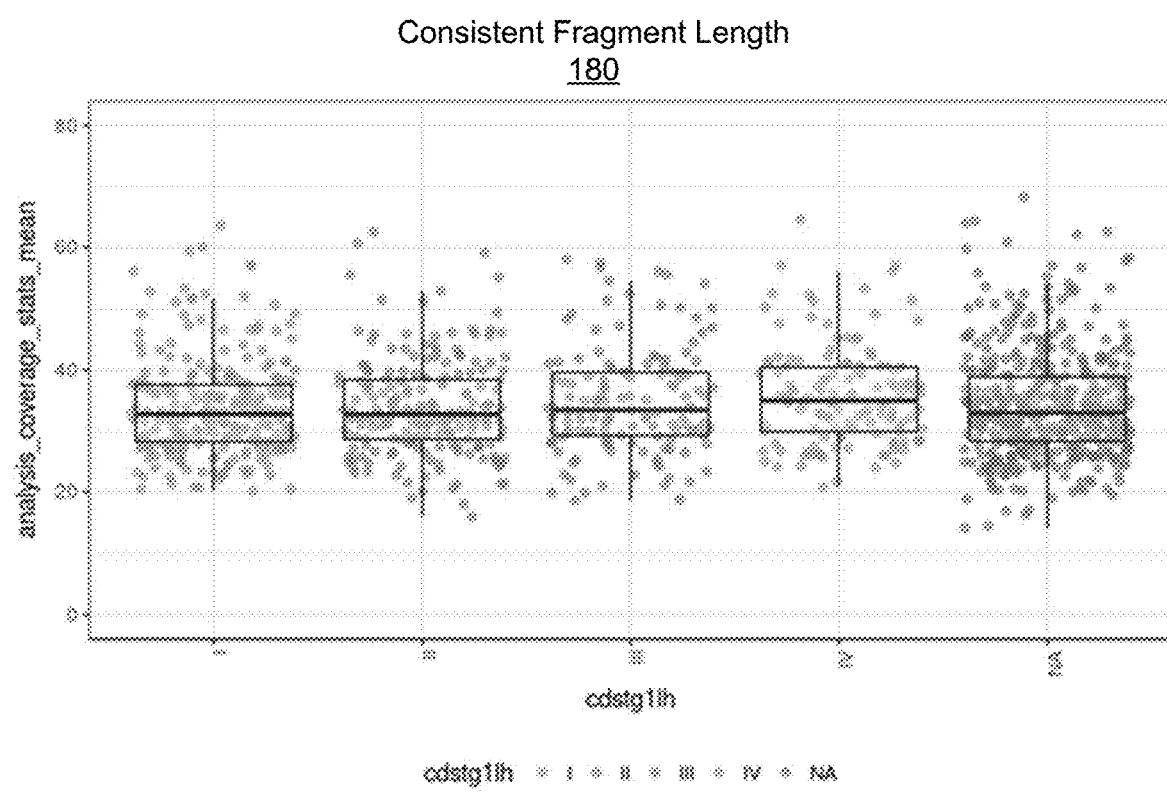
FIG. 1C

| CpG | 12 | 13 | 14 | 15 | 16 | 17 |
|---|---|---|---|---|---|---|
| Fragment A 222 — R1 | M | M | U | M | | |
| Fragment A 222 — R2 | | | U | M | M | M |
| Fragment B 224 — R1 | M | M | U | | | |
| Fragment B 224 — R2 | | | U | M | M | M |

FIG. 2B

| CpG | 12 | 13 | 14 | 15 | 16 | 17 |
|---|---|---|---|---|---|---|
| Fragment C 226 — R1 | M | M | V | M | | |
| Fragment C 226 — R2 | | | V | M | M | M |
| Fragment D 228 — R1 | M | M | M | | | |
| Fragment D 228 — R2 | | | | M | M | M |

|             | CpG | 12 | 13 | 14 | 15 | 16 | 17 |
|-------------|-----|----|----|----|----|----|----|
| Fragment E 232 | R1  | M  | M  | A  | M  |    |    |
|             | R2  |    |    |    | M  | M  | M  |
| Fragment F 234 | R1  | M  | M  | M  |    |    |    |
|             | R2  |    |    |    | M  | M  | M  |

|             | CpG | 12 | 13 | 14 | 15 | 16 | 17 |
|-------------|-----|----|----|----|----|----|----|
| Fragment G 236 | R1  | M  | M  |    |    |    |    |
|             | R2  |    |    | M  | M  | M  | M  |
| Fragment H 238 | R1  | M  | M  | U  |    |    |    |
|             | R2  |    |    |    | M  | M  | M  |

|            | CpG | 12 | 13 | 14 | 15 | 16 | 17 |
|------------|-----|----|----|----|----|----|----|
| Fragment I 242 | R1  | M  | M  | M  | M  |    |    |
|            | R2  |    |    | M  | M  | M  | M  |
| Fragment J 244 | R1  | M  | M  | U  |    |    |    |
|            | R2  |    |    |    | M  | M  | M  |

FIG. 2F

|            | CpG | 12 | 13 | 14 | 15 | 16 | 17 |
|------------|-----|----|----|----|----|----|----|
| Fragment K 246 | R1  | M  | M  | M  | M  |    |    |
|            | R2  |    |    | M  | M  | M  | M  |
| Fragment L 248 | R1  | M  | M  | U  |    |    |    |
|            | R2  |    |    | U  | M  | M  | M  |

FIG. 2G

Generate data structure for a control group
300

```
┌─────────────────────────────────────────────┐
│  Generate set of methylation state vectors  │
│            for a control group              │
│                    100                      │
└─────────────────────────────────────────────┘
                      ↓
┌─────────────────────────────────────────────┐
│ For each methylation state vector, subdivide│
│       into strings of methylation sites     │
│                    305                      │
└─────────────────────────────────────────────┘
                      ↓
┌─────────────────────────────────────────────┐
│  Tally strings for each position and        │
│         methylation state combination       │
│                    310                      │
└─────────────────────────────────────────────┘
                      ↓
┌─────────────────────────────────────────────┐
│  Create data structure storing counts of all│
│    possible strings from the control group  │
│                    315                      │
└─────────────────────────────────────────────┘
```

FIG. 3A

Training of Cancer Classifier
400

Obtain a plurality of training samples of varying cancer types, each training sample comprising a set of anomalous fragments and a label of cancer type
410

For each training sample, determine a feature vector based on the filtered set of anomalous fragments of the training sample
420

For each CpG site in the feature vectors, compute an information gain based on the feature vectors of the training samples
430

Select a set of CpG sites to consider based on the computed information gain
440

Modify feature vectors based on the selected set of CpG sites
450

Train the Cancer Classifier to distinguish between cancer and non-cancer based on the feature vectors of the training samples
460

Train the Cancer Classifier to distinguish between each cancer type based on the feature vectors of the training samples
470

FIG. 4

METHYLATION-BASED FALSE POSITIVE DUPLICATE MARKING REDUCTION

CROSS REFERENCE TO RELATED APPLICATIONS

This application claims the benefit of and priority to U.S. Provisional Application No. 62/828,899 filed Apr. 3, 2019, and entitled "Methylation-Based False Positive Duplicate Marking Reduction", which is incorporated by reference in its entirety.

BACKGROUND

Field of Art

DNA methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free DNA. However, there remains a need in the art for improved methods for analyzing methylation sequencing data from cell-free DNA for the detection, diagnosis, and/or monitoring of diseases, such as cancer.

SUMMARY

Early detection of cancer in subjects is important as it allows for earlier treatment and therefore a greater chance for survival. Sequencing of DNA fragments in cell-free (cf) DNA samples to determine methylation states of various dinucleotides of cytosine and guanine (known as CpG sites) in the fragments provides insight into whether a subject may have cancer, and further insight on what type of cancer the subject may have. Towards that end, systems and methods are presented for analyzing methylation states of CpG sites of DNA fragments for determining a subject's likelihood of having cancer. Furthermore, systems and methods are presented that describe identifying and removal of duplicate sequence reads, and/or methods for reducing incidents of fragments falsely marked as duplicates.

One embodiment of marking duplicate fragments is as follows. An analytics system identifies a first fragment and a second fragment as being derived from a matching location. The analytics system generates a first methylation state vector for the first fragment and a second methylation state vector for the second fragment, each methylation state vector comprising a methylation state for each of a set of CpG sites, each methylation state comprising one of: methylated, unmethylated, variant, and ambiguous. The analytics system, for each CpG site of the set of CpG sites, computes a difference score for the CpG site based on whether the methylation state at the CpG site included in the first methylation state vector agrees or disagrees with the methylation state at the CpG site included in the second methylation state vector. The analytics system computes a modified Hamming distance based on the computed difference scores. The analytics system, in response to the modified Hamming distance exceeding a threshold score, retains the first fragment and the second fragment as unique fragments; and, in response to the modified Hamming distance not exceeding the threshold score, labels the first fragment and the second fragment as duplicate fragments.

In a further embodiment, the first fragment comprises a first pair of sequence reads and the second fragment comprises a second pair of sequence reads, and wherein computing a difference score for a CpG site is based further on whether one or both methylation states at the CpG site within the first pair of sequence reads disagrees with one or both methylation states at the CpG site within the second pair of sequence reads.

In a further embodiment, a first difference score for a first CpG site with both methylation states within the first pair of sequence reads comprising a methylated state and at least one methylation states within the second pair of sequence reads comprising an unmethylated state is greater than a second difference score for a second CpG site in which only one methylation state within the first pair of sequence reads comprises a methylated state and only one methylation state within the second pair of sequence reads comprises an unmethylated state.

In a further embodiment, a difference score for a CpG site with a methylation state of methylated or unmethylated within the first methylation state vector is the same for a matching methylation state within the second methylation state vector, for a methylation state of variant within the second methylation state vector, and for a methylation state of ambiguous within the second methylation state vector.

In a further embodiment, a first difference score for a first CpG site with a methylation state of methylated within the first methylation state vector and the second methylation state vector is less than a second difference score for a second CpG site with a methylation state of methylated within the first methylation state vector and a methylation state of unmethylated within the second methylation state vector.

In a further embodiment, computing the modified Hamming distance comprises summing the computed difference scores for each CpG site in the set of CpG sites.

In a further embodiment, the first fragment and the second fragment are identified as being derived from the matching reference location if the first fragment and the second fragment have matching start reference locations and matching end reference locations.

In a further embodiment, the analytic system, in response to identifying the first fragment and the second fragment as duplicates, filters one of the first fragment and the second fragment.

In a further embodiment, the analytics system applies a cancer prediction model to fragments determined to be unique fragments to generate a cancer prediction for the test subject, the cancer prediction model configured to produce a likelihood of cancer for the test subject for each of one or more cancer types based at least in part on the methylation states of the unique fragments.

In a further embodiment, the analytics system filters an initial set of unique fragments with p-value filtering to generate a set of anomalous fragments, the filtering comprising removing fragments from the initial set having below a threshold p-value with respect to others to produce the set of anomalous fragments, wherein the cancer prediction model is applied to the set of anomalous fragments to generate the cancer prediction for the test subject.

In a further embodiment, each anomalous fragment is also hypomethylated or hypermethylated such that the anomalous fragment includes at least a threshold number of CpG sites with more than a threshold percentage of the CpG sites being unmethylated or with more than the threshold percentage of the CpG sites being methylated, respectively.

In a further embodiment, applying a cancer prediction model to the set of anomalous fragments to generate the cancer prediction for the test subject comprises 1) generating a test feature vector by generating for each of a plurality of CpG sites from a reference genome a score based on whether one or more of the anomalous fragments overlaps the CpG site; 2) inputting the test feature vector into the cancer prediction model to generate the cancer prediction for the test subject comprising a plurality of cancer prediction values, each cancer prediction value describing a likelihood the test sample is of a particular cancer type of the one or more cancer types, the cancer prediction model comprising: a plurality of classification parameters, and a function representing a relation between the test feature vector received as input and the cancer prediction generated as output based on the test feature vector and the classification parameters; and 3) determining whether or not the test subject has a first cancer type from the one or more cancer types based on the cancer prediction.

In a further embodiment, the cancer prediction model is a neural network having a plurality of layers including an input layer for receiving the test feature vector and an output layer for returning the cancer prediction based on the test feature vector, wherein the function and the classification parameters define edges between nodes of the plurality of layers.

In a further embodiment, the function of the cancer prediction model is one of a logistic regression, a multinomial regression, and a non-linear regression.

BRIEF DESCRIPTION OF DRAWINGS

FIGS. 1C & 1D show three graphs of data validating consistency of sequencing from a control group.

FIGS. 2B-2G show example difference score calculations for the process illustrated in FIG. 2A.

FIGS. 3A & 3B illustrate flowcharts describing a process of determining anomalously methylated fragments from a sample, according to an embodiment.

FIG. 4 is a flowchart describing a process of training a classifier, according to an embodiment.

Figure 1A:
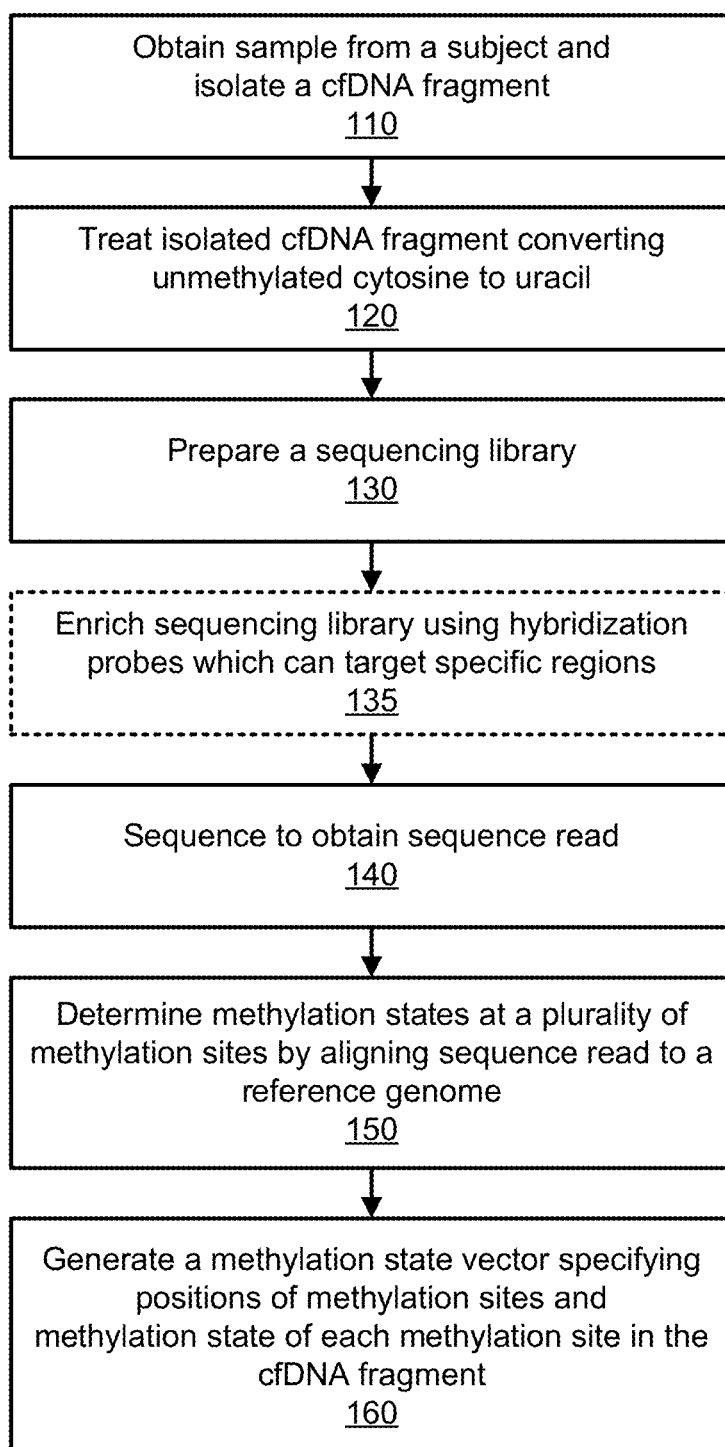
FIG. 1A is a flowchart describing a process of sequencing a fragment of cell-free (cf) DNA to obtain a methylation state vector, according to some embodiments.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. Overview

I.A. Overview of Methylation

In accordance with the present description, cfDNA fragments from an individual are treated, for example by converting unmethylated cytosines to uracils, sequenced and the sequence reads compared to a reference genome to identify the methylation states at specific CpG sites within the DNA fragments. Each CpG site may be methylated or unmethylated. Identification of anomalously methylated fragments, in comparison to healthy individuals, may provide insight into a subject's cancer status (see, e.g., U.S. 2019/0287652, entitled "Anomalous Fragment Detection and Classification," which is incorporated herein by reference). As is well known in the art, DNA methylation anomalies (compared to healthy controls) can cause different effects, which may contribute to cancer. Various challenges arise in the identification of anomalously methylated cfDNA fragments. For one, identifying unique fragments within a sample can be challenging due to numerous sources of potential discrepancies and errors. For example, one of two truly duplicate fragments in a sample may be sequenced and read as having varying methylation at one or more CpG sites. Both fragments may be identified as unique and retained for downstream analyses of the sample's methylation pattern. On the other hand, accidental marking of truly unique fragments (for instance, two fragments with the same start and end positions, but with different methylation patterns) as duplicate fragments can result in one of the unique fragments being removed from consideration. In both cases, imprecise marking of duplicate fragments can result in additional problems during downstream analyses and result in lower accuracy in disease classification.

Methylation typically occurs in deoxyribonucleic acid (DNA) when a hydrogen atom on the pyrimidine ring of a cytosine base is converted to a methyl group, forming 5-methylcytosine. In particular, methylation tends to occur at dinucleotides of cytosine and guanine referred to herein as "CpG sites". In other instances, methylation may occur at a cytosine not part of a CpG site or at another nucleotide that is not cytosine; however, these are rarer occurrences. In this present disclosure, methylation is discussed in reference to CpG sites for the sake of clarity. Anomalously methylated DNA molecules or fragments can be identified as hypermethylated or hypomethylated DNA molecules or fragments, both of which can be indicative of cancer status. Throughout this disclosure, hypermethylation and hypomethylation is characterized for a DNA fragment, if the DNA fragment comprises more than a threshold number of CpG sites with more than a threshold percentage of those CpG sites being methylated or unmethylated.

Those of skill in the art will appreciate that the principles described herein are equally applicable for the detection of methylation in a non-CpG context, including non-cytosine methylation. In such embodiments, the wet laboratory assay used to detect methylation may vary from those described herein. Further, the methylation state vectors discussed herein may contain elements that are generally sites where methylation has or has not occurred (even if those sites are not CpG sites specifically). With that substitution, the remainder of the processes described herein are the same, and consequently the inventive concepts described herein are applicable to those other forms of methylation.

I.B. Definitions

The term "individual" refers to a human individual. The term "healthy individual" refers to an individual presumed or known to not have a cancer or disease. The term "subject" refers to an individual who is known to have, or potentially has, a cancer or disease.

The term "cell free nucleic acid" or "cfNA" refers to nucleic acid fragments that circulate in an individual's body (e.g., blood) and originate from one or more healthy cells and/or from one or more cancer cells. The term "cell free DNA," or "cfDNA" refers to deoxyribonucleic acid fragments that circulate in an individual's body (e.g., blood). Additionally cfNAs or cfDNA in an individual's body may come from other non-human sources.

The term "genomic nucleic acid," "genomic DNA," or "gDNA" refers to nucleic acid molecules or deoxyribonucleic acid molecules obtained from one or more cells. In various embodiments, gDNA can be extracted from healthy cells (e.g., non-tumor cells) or from tumor cells (e.g., a biopsy sample). In some embodiments, gDNA can be extracted from a cell derived from a blood cell lineage, such as a white blood cell.

The term "circulating tumor DNA" or "ctDNA" refers to nucleic acid fragments that originate from tumor cells or other types of cancer cells, and which may be released into a bodily fluid of an individual (e.g., blood, sweat, urine, or saliva) as result of biological processes such as apoptosis or necrosis of dying cells or actively released by viable tumor cells.

The term "DNA fragment," "fragment," or "DNA molecule" may generally refer to any deoxyribonucleic acid fragments, i.e., cfDNA, gDNA, ctDNA, etc. For example, a DNA molecule can be broken up, or fragmented into, a plurality of segments, either through natural processes, as is the case with, e.g., cfDNA fragments that can naturally occur within a biological sample, or through in vitro manipulation (e.g., known chemical, mechanical or enzymatic fragmentation methods). In some embodiments, as one of skill in the art would readily appreciate, and as described herein, methylation status at one or more methylation sites (e.g., CpG sites) in a fragment can be determined, or inferred, from one or more sequence reads derived from the fragment. For example, the nucleotide base sequence of a DNA fragment or molecule can be determined from sequence reads derived from the DNA fragment, and thus, methylation status at one or more methylation sites (e.g., CpG sites) in the original fragment determined or inferred. Accordingly, "fragment" and "sequence read" can be used interchangeably herein.

The term "sequence read" refers to a nucleotide sequence obtained from a nucleic acid molecule from a test sample from an individual. Sequence reads can be obtained through various methods known in the art. The term "read pair" refers to a pair of sequence reads (that may be identified as read 1 and read 2) corresponding to opposing sequencing directions of a DNA fragment, i.e., 3' to 5' and 5' to 3'.

The term "sequencing depth" or "depth" refers to a total number of sequence reads or read segments at a given genomic location or loci from a test sample from an individual.

The term "anomalous fragment," "anomalously methylated fragment," or "fragment with an anomalous methylation pattern" refers to a fragment that has anomalous methylation of CpG sites. Anomalous methylation of a fragment may be determined using probabilistic models to identify unexpectedness of observing a fragment's methylation pattern in a control group.

The term "unusual fragment with extreme methylation" or "UFXM" refers to a hypomethylated fragment or a hypermethylated fragment. A hypomethylated fragment and a hypermethylated fragment refers to a fragment with at least some number of CpG sites (e.g., 5) that have over some threshold percentage (e.g., 90%) of methylation or unmethylation, respectively.

The term "anomaly score" refers to a score for a CpG site based on a number of anomalous fragments (or, in some embodiments, UFXMs) from a sample overlaps that CpG site. The anomaly score is used in context of featurization of a sample for classification.

II. Sample Processing

II.A. Generating Methylation State Vectors for DNA Fragments

FIG. 1A is a flowchart describing a process 100 of sequencing a fragment of cell-free (cf) DNA to obtain a methylation state vector, according to an embodiment. In order to analyze DNA methylation, an analytics system first obtains 110 a sample from an individual comprising a plurality of cfDNA molecules. Generally, samples may be from healthy individuals, subjects known to have or suspected of having cancer, or subjects where no prior information is known. The test sample may be a sample selected from the group consisting of blood, plasma, serum, urine, fecal, and saliva samples. Alternatively, the test sample may comprise a sample selected from the group consisting of whole blood, a blood fraction (e.g., white blood cells (WBCs)), a tissue biopsy, pleural fluid, pericardial fluid, cerebral spinal fluid, and peritoneal fluid. In additional embodiments, the process 100 may be applied to sequence other types of DNA molecules (e.g., nuclear DNA (nDNA) extracted from white blood cells (WBCs) or a tissue biopsy sample).

From the sample, the analytics system isolates each cfDNA molecule. The cfDNA molecules are treated to convert unmethylated cytosines to uracils, while leaving methylated cytosines unconverted. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted cfDNA molecules, a sequencing library is prepared 130. Optionally, the sequencing library may be enriched 135 for cfDNA molecules, or genomic regions, that are informative for cancer status using a plurality of hybridization probes (see, e.g., WO 2019/195268, entitled "Methylation Markers and Targeted Methylation Probe Panels," which is incorporated herein by reference). The hybridization probes are short oligonucleotides capable of hybridizing to particularly specified cfDNA molecules, or more specifically, cfDNA molecules derived from targeted regions, and enriching for those fragments for subsequent sequencing and analysis. Hybridization probes may be used to perform a targeted, high-depth analysis of a set of specified CpG sites of interest to the researcher. In one embodiment, the hybridization probes are designed to enrich for DNA molecules that have been treated (e.g., using bisulfite) for conversion of unmethylated cytosines to uracils, and thus, specifically target cfDNA fragments derived from cancer cells based on expected methylation status observed in cancer samples (again, see, e.g., WO 2019/195268). Once prepared, the sequencing library or a portion thereof can be sequenced to obtain a plurality of sequence reads. The sequence reads may be in a computer-readable, digital format for processing and interpretation by computer software.

From the sequence reads, the analytics system determines 150 a location and methylation state for each CpG site based on alignment to a reference genome. In order to accomplish this, the analytics system generates a methylation state vector for each sequence read in the fragment's read pair whether methylated (e.g., denoted as M), unmethylated (e.g., denoted as U), or variant (e.g., describing a read of something not corresponding to the intended CpG site denoted as V, also referred to as indeterminate). With the methylation state vectors from the sequence reads in a read pair, the analytics system generates a methylate state vector for the fragment including the methylation states of each sequence read in the read pair. If there is a consensus between states of the read pair at a CpG site, then the consensus state is included in the methylation state vector for the fragment at that CpG site. If only one of the two sequence reads has a methylation state at a CpG site, then the state is included in the methylation state vector for the fragment at that CpG site. If there is a disagreement between methylation states of the read pair at a CpG site, then a state of ambiguous (e.g., denoted as A) is assigned to that CpG site for the fragment's methylation state vector. The methylation state vectors may be stored in temporary or persistent computer memory for later use and processing.

Further, the analytics system may remove duplicate reads or duplicate methylation state vectors from a single sample. Duplicate fragments can originate in different manners. One manner in which duplicate fragments may arise is during polymerase chain reaction (PCR) amplification. During PCR amplification, a single DNA fragment in a sample may be amplified many times over with potential of multiple copies of the DNA fragment being sequenced giving rise to PCR duplicates. Another manner where duplicates may originate comes from various mechanisms involved in sequencing DNA fragments to achieve sequence reads. These duplicates may be termed optical duplicates. For example, when using patterned flow cells, large clusters may be mistakenly called by the sequencer as distinct clusters, i.e., distinct sequence reads. In another example with patterned flow cells, a single DNA fragment may bind to one or more nanowells in the flow cell thereby creating multiple clusters that are read as distinct sequence reads despite originating from the single DNA fragment. Precise marking of duplicate fragments improves efficiency and performance of downstream analyses. Conventionally, duplicate fragments are marked according to fragments that match in location, i.e., same sequencing start reference location and same sequencing end reference location for the fragments. However, these conventional methods result in many marked false positives, i.e., many truly non-duplicate fragments marked as duplicate. A process for marking duplicate fragments while reducing the number of false positive duplicates will be described below in FIGS. 2A-2G.

In some embodiments, the analytics system may groom fragments having too sparse methylation data. The analytics system may determine that a certain fragment is too sparse in methylation information if over a threshold number or percentage of CpG sites have indeterminate methylation statuses, and can exclude such fragments or selectively include such fragments by build a model accounting for such indeterminate methylation statuses; one such model will be described below in conjunction with FIG. 4.

Figure 1B:
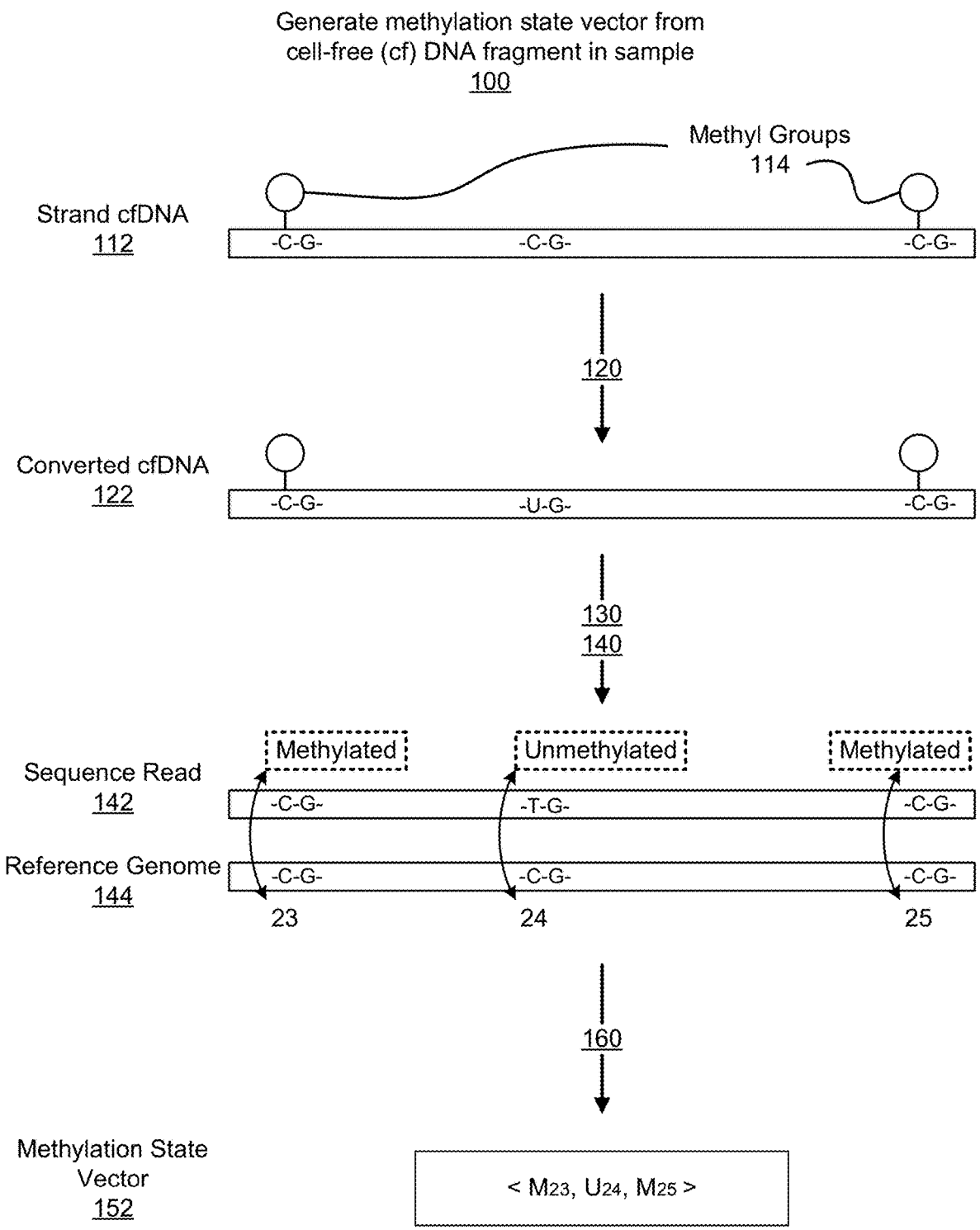
FIG. 1B is an illustration of the process of FIG. 1A of sequencing a fragment of cell-free (cf) DNA to obtain a methylation state vector, according to some embodiments.

FIG. 1B is an illustration of the process 100 of FIG. 1A of sequencing a cfDNA molecule to obtain a methylation state vector, according to an embodiment. As an example, the analytics system receives a cfDNA molecule 112 that, in this example, contains three CpG sites. As shown, the first and third CpG sites of the cfDNA molecule 112 are methylated 114. During the treatment step 120, the cfDNA molecule 112 is converted to generate a converted cfDNA molecule 122. During the treatment 120, the second CpG site which was unmethylated has its cytosine converted to uracil. However, the first and third CpG sites were not converted.

After conversion, a sequencing library 130 is prepared and sequenced 140 generating a sequence read 142. The analytics system aligns 150 the sequence read 142 to a reference genome 144. The reference genome 144 provides the context as to what position in a human genome the fragment cfDNA originates from. In this simplified example, the analytics system aligns 150 the sequence read 142 such that the three CpG sites correlate to CpG sites 23, 24, and 25 (arbitrary reference identifiers used for convenience of description). The analytics system thus generates information both on methylation status of all CpG sites on the cfDNA molecule 112 and the position in the human genome that the CpG sites map to. As shown, the CpG sites on sequence read 142 which were methylated are read as cytosines. In this example, the cytosines appear in the sequence read 142 only in the first and third CpG site which allows one to infer that the first and third CpG sites in the original cfDNA molecule were methylated. Whereas, the second CpG site is read as a thymine (U is converted to T during the sequencing process), and thus, one can infer that the second CpG site was unmethylated in the original cfDNA molecule. With these two pieces of information, the methylation status and location, the analytics system generates 160 a methylation state vector 152 for the fragment cfDNA 112. In this example, the resulting methylation state vector 152 is $<M_{23}, U_{24}, M_{25}>$, wherein M corresponds to a methylated CpG site, U corresponds to an unmethylated CpG site, and the subscript number corresponds to a position of each CpG site in the reference genome.

Figure 1D:
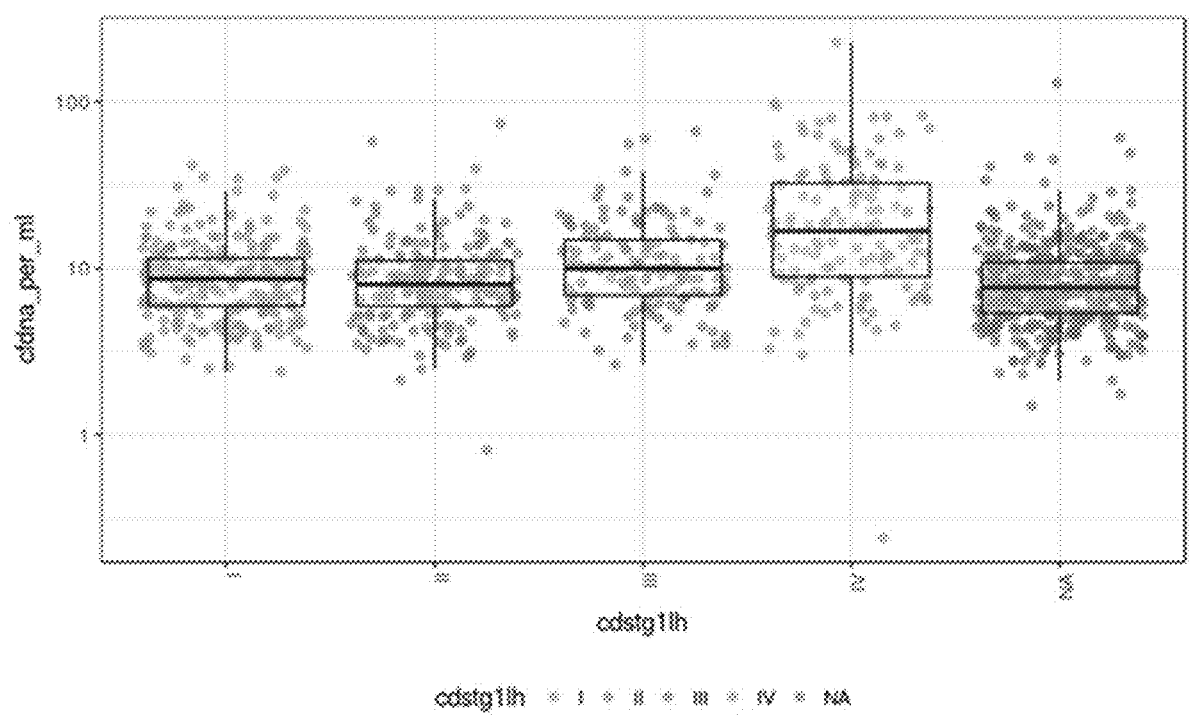

FIGS. 1C & 1D show three graphs of data validating consistency of sequencing from a control group. The graph 170 in FIG. 1C shows example results of conversion accuracy of unmethylated cytosines to uracil (step 120) on cfDNA molecule obtained from a test sample across subjects in varying stages of cancer—stage I, stage II, stage III, stage IV, and non-cancer. As shown, there was uniform consistency in converting unmethylated cytosines on cfDNA molecules into uracils. There was an overall conversion accuracy of 99.47% with a precision at ±0.024%. The graph 180 in FIG. 1C shows example results of mean coverage over varying stages of cancer. The mean coverage over all groups being ~34× mean across the genome coverage of DNA molecules, using only those confidently mapped to the genome are counted. The graph 190 in FIG. 1D shows example results of concentration of cfDNA per sample across varying stages of cancer.

II.B. Identifying Duplicate Fragments

Figure 2A:
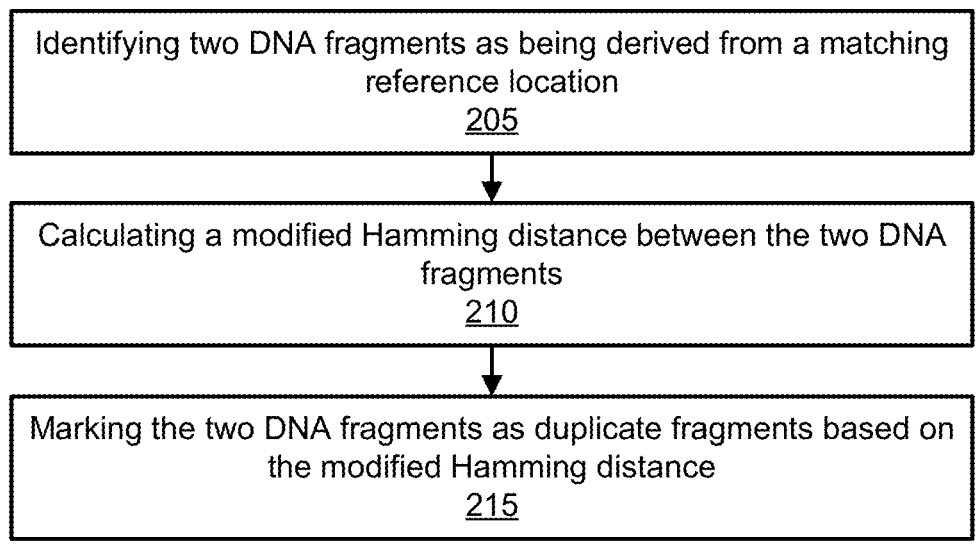
FIG. 2A is a flowchart describing a process of marking duplicate fragments, according to some embodiments.

FIG. 2A is a flowchart describing a process 200 of marking duplicate DNA fragments, according to some embodiments. The process 200 of marking of duplicate DNA fragments may be implemented in a context, e.g., by the analytics system, of identifying unique DNA fragments sequenced for a sample. The process 200 balances specificity in avoiding false positives, i.e., truly non-duplicate fragments marked as duplicate, and sensitivity in avoiding false negatives, i.e., failing to mark truly duplicate fragments. The analytics system obtains methylation state vectors from the plurality of DNA fragments in a sample.

The analytics system identifies 205 two DNA fragments as being derived from a matching reference location. In one embodiment, a matching reference location refers to fragments with matching sequencing start reference locations and matching sequencing end reference locations. For instance during the course of checking each fragment's sequencing start and end reference locations against other fragments in the sample, the analytics system identifies the two DNA fragments as having matching locations. In some embodiments, two DNA fragments can be identified as having matching locations when the nucleotide at one or both of the start and/or end reference locations match. However, as one of skill in the art would readily appreciate, the nucleotides at the start and end locations do not need to match exactly for two fragments to be identified as originating from the same location. For example, in some embodiments, two DNA fragments can be identified as having matching locations when the start and end reference positions differ by one or more nucleotides at either or both of the start or end reference locations (e.g., from 1 to 3 nucleotides on either end of the fragments may be a different nucleotide base or could be missing (i.e., trimmed off from the end) from the DNA molecule and/or resulting sequence read). Conventional methods for marking duplicate fragments mark DNA fragments that match in location as duplicates. However, these conventional methods fail to consider the methylation states of DNA fragments that have matching locations giving way to unnecessary false positives.

The analytics system calculates 210 a modified Hamming distance between the two DNA fragments. The analytics system considers methylation states included in the methylation state vectors of the two DNA fragments. The analytics system may further consider methylation states of each sequence read in the pair of sequence reads used to derive the methylation state vector for the DNA fragment. To compute the modified Hamming distance, the analytic system assigns a difference score for each CpG site of the two DNA fragments based on a comparison of the methylation states at that CpG site within the methylation state vectors. The difference score may additionally be based on a consideration of the methylation states at each CpG site among each pair of sequence reads. The difference score at any given CpG site indicates a degree of difference between the methylation states of the two fragments at that CpG site. The analytics system calculates the modified Hamming distance between two DNA fragments as a sum of the difference scores between the common CpG sites between the fragments, the modified Hamming distance indicating a total degree of difference between the methylation states of the two fragments at the common CpG sites. In some embodiments, the analytics system takes into account length of fragments (e.g., number of base pairs, number of CpG sites, etc.) in calculating the modified Hamming distance. As an example, the analytics system may normalize the modified Hamming distances according to length.

According to one or more embodiments, the analytics system assigns difference scores as follows. If the analytics system determines that all corresponding methylation states included in the two methylation state vectors either agree or are not in conflict, the analytics system assigns a difference score of 0 (for instance, as illustrated in FIG. 2B, described below). If the analytics system determines that one or more corresponding methylation states included in the two methylation state vectors disagree, the analytics system further assesses the disagreement. If the disagreement is the result of a methylation state in a first of the methylation state vectors including a variant state or an ambiguous state, then the analytics system assigns a difference score of 0 (for instance, as illustrated in FIGS. 2C and 2D, described below). If the disagreement is the result of a first methylation vector including a methylated state and a second methylation vector including a corresponding unmethylated state, the analytics system assigns a difference score of 1 (for instance, as illustrated in FIG. 2E, described below). In additional embodiments, the analytics system further considers the sequence reads in each read pair of the fragments. If both sequence reads in the sequence read pair of a first fragment include a methylated state, and one of the sequence reads in the sequence read pair of a second fragment include an unmethylated state, the analytics system assigns a difference score of 2 (as illustrated in FIG. 2F, described below). If both sequences reads in a sequence read pair of a first fragment include a methylated state, and both sequences reads in a second read pair of a second fragment include an unmethylated state, the analytics system assigns a difference score of 4 (for instance, as illustrated in FIG. 2G, described below). The analytics system assigns a difference score to the two fragments for each methylation state within the methylation state vectors of the two fragments, and then computes the modified Hamming distance based on the sum of the assigned difference scores.

FIGS. 2B-2G show example difference score calculations based on the process shown in FIG. 2A. In each example, two DNA fragments have been identified as having methylation state vectors with matching locations, e.g., at CpG sites 12, 13, 14, 15, 16, and 17 within an example reference genome. Each fragment's methylation state vector includes methylations states that are determined from the sequence read pair of the fragment.

FIG. 2B shows two methylation state vectors for CpG sites of fragment A 222 and fragment B 224. The methylation state vector for fragment A 222 in FIG. 2B is <$M_{12}$, $M_{13}$, $U_{14}$, $M_{15}$, $M_{16}$, $M_{17}$>. The methylation state vector for fragment B 224 in FIG. 2B is <$M_{12}$, $M_{13}$, $U_{14}$, $M_{15}$, $M_{16}$, $M_{17}$>. Because the methylation states of the two methylation state vectors for fragment A 222 and fragment B 224 are in agreement at each CpG site, the analytics system assigns a difference score of 0 to fragment A 222 and fragment B 224.

FIG. 2C shows methylation state vectors for CpG sites of fragment C 226 and fragment D 228. The methylation state vector for fragment C 226 in FIG. 2C is <$M_{12}$, $M_{13}$, $V_{14}$, $M_{15}$, $M_{16}$, $M_{17}$>. The methylation state vector for fragment D 228 in FIG. 2C is <$M_{12}$, $M_{13}$, $M_{14}$, $M_{15}$, $M_{16}$, $M_{17}$>. The methylation states of the two methylation state vectors for fragment A 222 and fragment B 224 at CpG sites 12-13 and 15-17 are in agreement, and the analytics system assigns a difference score of 0 for these CpG sites. However, at CpG site 14, the analytic system identifies a disagreement 220 between the two fragments, i.e., fragment C 226 has a methylation state of variant and fragment D 228 has a methylation state of methylated. As noted above, in the embodiment where the disagreement stems from a variant state and a methylated state, the analytics system assigns a difference score for the CpG site 14 of 0.

FIG. 2D shows methylation state vectors for CpG sites of fragment E 232 and fragment F 234. The methylation state vector for fragment E 232 in FIG. 2D is <$M_{12}, M_{13}, A_{14}, M_{15}, M_{16}, M_{17}$>. The methylation state vector for fragment F 234 in FIG. 2D is <$M_{12}, M_{13}, M_{14}, M_{15}, M_{16}, M_{17}$>. The methylation states of the two methylation state vectors for fragment E 232 and fragment F 234 at CpG sites 12-13 and 15-17 are in agreement, and the analytics system assigns a difference score of 0 for these CpG sites. However, at CpG site 14, the analytic system identifies a disagreement 230 between the two fragments, i.e., fragment E 232 has a methylation state of ambiguous and fragment F 234 has a methylation state of methylated. As noted above, in the embodiment where the disagreement stems from an ambiguous state and a methylated state, the analytics system assigns a difference score for the CpG site 14 of 0.

FIG. 2E shows methylation state vectors for CpG sites of fragment G 236 and fragment H 238. The methylation state vector for fragment G 236 in FIG. 2E is <$M_{12}, M_{13}, M_{14}, M_{15}, M_{16}, M_{17}$>. The methylation state vector for fragment H 238 in FIG. 2E is <$M_{12}, M_{13}, U_{14}, M_{15}, M_{16}, M_{17}$>. The methylation states of the two methylation state vectors for fragment G 236 and fragment H 238 at CpG sites 12-13 and 15-17 are in agreement, and the analytics system assigns a difference score of 0 for these CpG sites. However, at CpG site 14, the analytic system identifies a disagreement 240 between the two fragments, i.e., fragment G 236 has a methylation state of methylated and fragment H 238 has a methylation state of unmethylated. As noted above, in the embodiment where the disagreement stems from a methylated state and an unmethylated state, the analytics system assigns a difference score of 1 for CpG site 14. In additional embodiments, the analytics system further considers the sequence reads of each fragment. In the embodiment of FIG. 2E, only one of each sequence read pair (e.g., R2 for fragment G 236 and R1 for fragment H 238) includes a respective methylation state, and so the assigned difference score of 1 for CpG site 14 remains unchanged.

FIG. 2F shows methylation state vectors for CpG sites of fragment I 242 and fragment J 244. The methylation state vector for fragment I 242 in FIG. 2F is <$M_{12}, M_{13}, M_{14}, M_{15}, M_{16}, M_{17}$>. The methylation state vector for fragment J 244 in FIG. 2F is <$M_{12}, M_{13}, U_{14}, M_{15}, M_{16}, M_{17}$>. The methylation states of the two methylation state vectors for fragment I 242 and fragment J 244 at CpG sites 12-13 and 15-17 are in agreement, and the analytics system assigns a difference score of 0 for these CpG sites. However, at CpG site 14, the analytic system identifies a disagreement 250 between the two fragments, i.e., fragment I 242 has a methylation state of methylated and fragment J 244 has a methylation state of unmethylated. As noted above, in the embodiment where the disagreement stems from a methylated state and an unmethylated state, the analytics system assigns a difference score of 1 for CpG site 14. However, in the embodiment of FIG. 2F, both sequence reads (R1 and R2) of fragment I 242 include the methylation state of methylated, and only one sequence read of fragment J 244 includes the methylation of unmethylated. Accordingly, the analytics system assigns a difference score of 2 for CpG site 14.

FIG. 2G shows methylation state vectors for CpG sites of fragment K 246 and fragment L 248. The methylation state vector for fragment K 246 in FIG. 2G is <$M_{12}, M_{13}, M_{14}, M_{15}, M_{16}, M_{17}$>. The methylation state vector for fragment L 248 in FIG. 2G is <$M_{12}, M_{13}, U_{14}, M_{15}, M_{16}, M_{17}$>. The methylation states of the two methylation state vectors for fragment K 246 and fragment L 248 at CpG sites 12-13 and 15-17 are in agreement, and the analytics system assigns a difference score of 0 for these CpG sites. However, at CpG site 14, the analytics system identifies a disagreement 260 between the two fragments, i.e., fragment K 246 has a methylation state of methylated and fragment L 248 has a methylation state of unmethylated. As noted above, because both sequence reads of fragment K 246 and fragment L 248 include a methylated state and an unmethylated state, respectively, the analytics system assigns a difference score of 4 for CpG site 14. Although not illustrated herein, in embodiments where both sequence reads for a first fragment include a methylated state at two CpG sites, and both sequence reads for a second fragment include an unmethylated state at the same two CpG sites, the analytics system assigns a difference score of 8 for the two fragments.

Returning to the process 200 of FIG. 2A, the analytics system marks 215 the two DNA fragments as duplicate fragments or as unique fragments based on the modified Hamming distance. The analytics system may set varying modified Hamming distance thresholds to tune between specificity and sensitivity in marking fragments as duplicates. Generally, a higher threshold may increase sensitivity but decrease specificity in marking duplicate fragments. Conversely, a lower threshold may generally increase specificity but decrease sensitivity in marking duplicate fragments. The analytics system determines whether a pair of DNA fragments have a modified Hamming distance less than (e.g., or less than or equal to) the Hamming distance threshold. If so, the analytics system marks that pair of DNA fragments as duplicate fragments. If not, the analytics system marks that pair of DNA fragments as non-duplicate or unique fragments. For example, for a modified Hamming distance threshold of 2, if the modified Hamming distance of a pair of DNA fragments is 1, then the analytics system marks the pair of DNA fragments as duplicate fragments. The analytics system may filter duplicate fragments and retain unique fragments. The analytics system may iterate through the process 200 for all fragments until no two fragments are duplicates.

In additional embodiments, the analytics system sorts candidate duplicate fragments into sets based on common start and end locations, as described above. Within each set of candidate duplicate fragments, the analytics system identifies a primary fragment within each set and iterates through the process 200 with the primary fragment and each of the other fragments in the set. Fragments marked as duplicate relative to the primary fragment are eliminated from consideration, while unique fragments are collated into a new set. The analytics system then iterates the process 200 for the new set (e.g., comparing a primary fragment within the new set to all other fragments in the new set), eliminating duplicates and moving unique fragments into yet another new set. The analytics system can continue this process until no set of fragments included more than one fragment, thereby eliminating all duplicates while avoiding false positive duplicates.

III. Identifying Anomalous Fragments

In some embodiments, the analytics system determines anomalous fragments for a sample using the sample's methylation state vectors (again, e.g., see U.S. 2019/0287652). For each fragment in a sample, the analytics system determines whether the fragment is an anomalous fragment using the methylation state vector corresponding to the fragment. Fragments in the sample may be retained from marking and removing duplicate fragments according to principles describe in Section II.B. In one embodiment, the analytics system calculates a p-value score for each methylation state vector describing a probability of observing that methylation state vector or other methylation state vectors even less probable in the healthy control group. The process for calculating a p-value score will be further discussed below in Section III.A. P-Value Filtering. The analytics system may determine fragments with a methylation state vector having below a threshold p-value score as anomalous fragments. In another embodiment, the analytics system further labels fragments with at least some number of CpG sites that have over some threshold percentage of methylation or unmethylation as hypermethylated and hypomethylated fragments, respectively, as described in Section III.B. A hypermethylated fragment or a hypomethylated fragment may also be referred to as an unusual fragment with extreme methylation (UFXM). In other embodiments, the analytics system may implement various other probabilistic models for determining anomalous fragments. Examples of other probabilistic models include a mixture model, a deep probabilistic model, etc. In some embodiments, the analytics system may use any combination of the processes described below for identifying anomalous fragments. With the identified anomalous fragments, the analytics system may filter the set of methylation state vectors for a sample for use in other processes, e.g., for use in training and deploying a cancer classifier.

III.A. P-Value Filtering

Figure 3B:
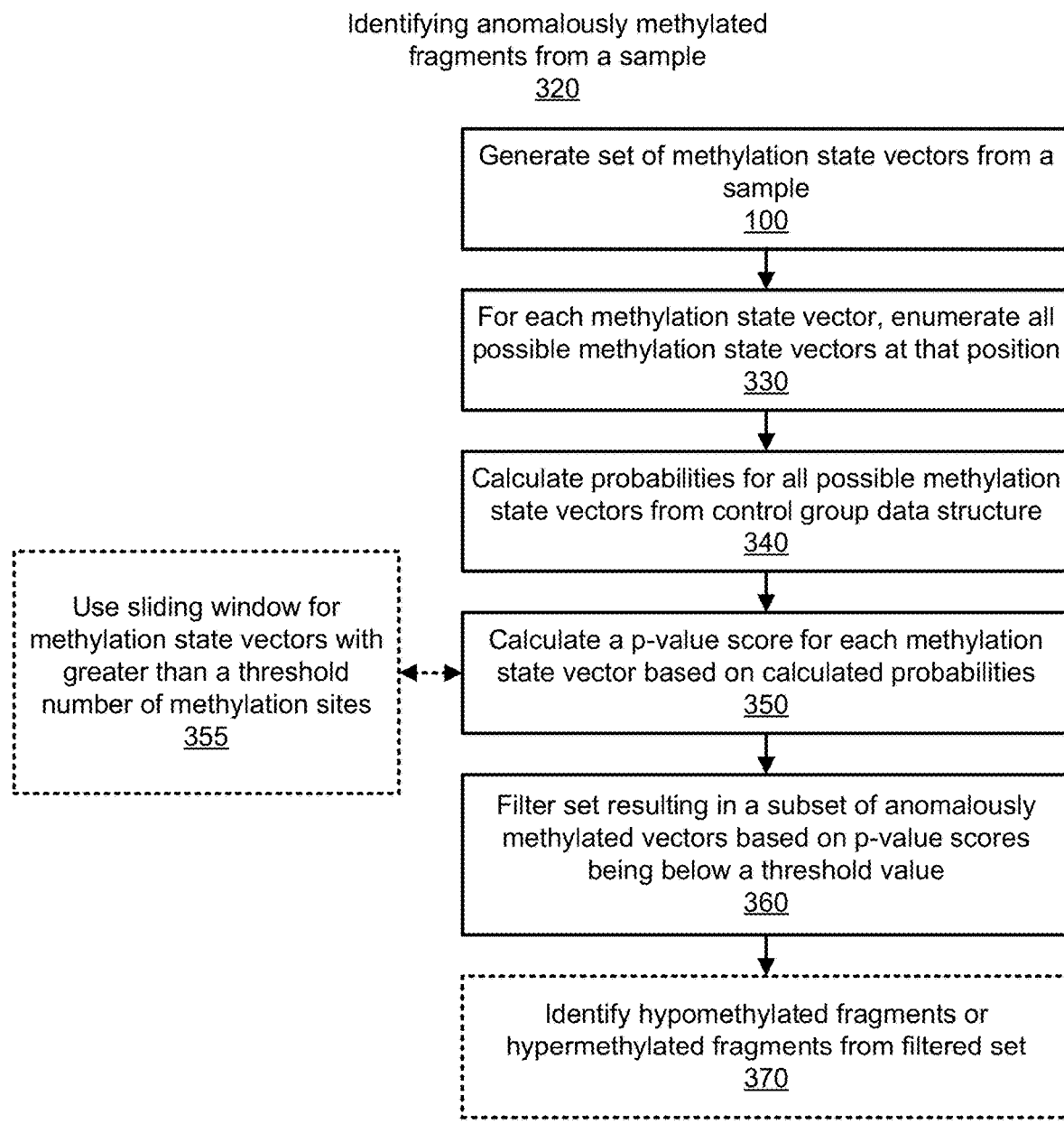

In one embodiment, the analytics system calculates a p-value score for each methylation state vector compared to methylation state vectors from fragments in a healthy control group. The p-value score describes a probability of observing the methylation status matching that methylation state vector or other methylation state vectors even less probable in the healthy control group. In order to determine a DNA fragment to be anomalously methylated, the analytics system uses a healthy control group with a majority of fragments that are normally methylated. When conducting this probabilistic analysis for determining anomalous fragments, the determination holds weight in comparison with the group of control subjects that make up the healthy control group. To ensure robustness in the healthy control group, the analytics system may select some threshold number of healthy individuals to source samples including DNA fragments. FIG. 3A below describes the method of generating a data structure for a healthy control group with which the analytics system may calculate p-value scores. FIG. 3B describes the method of calculating a p-value score with the generated data structure.

FIG. 3A is a flowchart describing a process 300 of generating a data structure for a healthy control group, according to an embodiment. To create a healthy control group data structure, the analytics system receives a plurality of DNA fragments (e.g., cfDNA) from a plurality of healthy individuals. A methylation state vector is identified for each fragment, for example via the process 100.

With each fragment's methylation state vector, the analytics system subdivides 305 the methylation state vector into strings of CpG sites. In one embodiment, the analytics system subdivides 305 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 would result in 4 strings of length 4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system tallies 310 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are $2^3$ or 8 possible string configurations. At that given CpG site, for each of the 8 possible string configurations, the analytics system tallies 310 how many occurrences of each methylation state vector possibility come up in the control group. Continuing this example, this may involve tallying the following quantities: $<M_x, M_{x+1}, M_{x+2}>, <M_x, M_{x+1}, U_{x+2}>, \ldots <U_x, U_{x+1}, U_{x+2}>$ for each starting CpG site x in the reference genome. The analytics system creates 315 the data structure storing the tallied counts for each starting CpG site and string possibility.

There are several benefits to setting an upper limit on string length. First, depending on the maximum length for a string, the size of the data structure created by the analytics system can dramatically increase in size. For instance, maximum string length of 4 means that every CpG site has at the very least $2^4$ numbers to tally for strings of length 4. Increasing the maximum string length to 5 means that every CpG site has an additional $2^4$ or 16 numbers to tally, doubling the numbers to tally (and computer memory required) compared to the prior string length. Reducing string size helps keep the data structure creation and performance (e.g., use for later accessing as described below), in terms of computational and storage, reasonable. Second, a statistical consideration to limiting the maximum string length is to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it requires a significant amount of data that may not be available, and thus would be too sparse for a model to perform appropriately. For example, calculating a probability of anomalousness/cancer conditioned on the prior 100 CpG sites would require counts of strings in the data structure of length 100, ideally some matching exactly the prior 100 methylation states. If only sparse counts of strings of length 100 are available, there will be insufficient data to determine whether a given string of length of 100 in a test sample is anomalous or not.

FIG. 3B is a flowchart describing a process 320 for identifying anomalously methylated fragments from an individual, according to an embodiment. In process 320, the analytics system generates 100 methylation state vectors from cfDNA fragments of the subject. The analytics system handles each methylation state vector as follows.

For a given methylation state vector, the analytics system enumerates 330 all possibilities of methylation state vectors having the same starting CpG site and same length (i.e., set of CpG sites) in the methylation state vector. As each methylation state is generally either methylated or unmethylated there are effectively two possible states at each CpG site, and thus the count of distinct possibilities of methylation state vectors depends on a power of 2, such that a methylation state vector of length n would be associated with $2^n$ possibilities of methylation state vectors. With methylation state vectors inclusive of indeterminate states for one or more CpG sites, the analytics system may enumerate 330 possibilities of methylation state vectors considering only CpG sites that have observed states.

The analytics system calculates 340 the probability of observing each possibility of methylation state vector for the identified starting CpG site and methylation state vector length by accessing the healthy control group data structure. In one embodiment, calculating the probability of observing a given possibility uses a Markov chain probability to model the joint probability calculation. In other embodiments, calculation methods other than Markov chain probabilities are used to determine the probability of observing each possibility of methylation state vector.

The analytics system calculates 350 a p-value score for the methylation state vector using the calculated probabilities for each possibility. In one embodiment, this includes identifying the calculated probability corresponding to the possibility that matches the methylation state vector in question. Specifically, this is the possibility having the same set of CpG sites, or similarly the same starting CpG site and length as the methylation state vector. The analytics system sums the calculated probabilities of any possibilities having probabilities less than or equal to the identified probability to generate the p-value score.

This p-value represents the probability of observing the methylation state vector of the fragment or other methylation state vectors even less probable in the healthy control group. A low p-value score, thereby, generally corresponds to a methylation state vector which is rare in a healthy individual, and which causes the fragment to be labeled anomalously methylated, relative to the healthy control group. A high p-value score generally relates to a methylation state vector is expected to be present, in a relative sense, in a healthy individual. If the healthy control group is a non-cancerous group, for example, a low p-value indicates that the fragment is anomalous methylated relative to the non-cancer group, and therefore possibly indicative of the presence of cancer in the test subject.

As above, the analytics system calculates p-value scores for each of a plurality of methylation state vectors, each representing a cfDNA fragment in the test sample. To identify which of the fragments are anomalously methylated, the analytics system may filter 360 the set of methylation state vectors based on their p-value scores. In one embodiment, filtering is performed by comparing the p-values scores against a threshold and keeping only those fragments below the threshold. This threshold p-value score could be on the order of 0.1, 0.01, 0.001, 0.0001, or similar.

According to example results from the process 320, the analytics system yields a median (range) of 2,800 (1,500-12,000) fragments with anomalous methylation patterns for participants without cancer in training, and a median (range) of 3,000 (1,200-220,000) fragments with anomalous methylation patterns for participants with cancer in training. These filtered sets of fragments with anomalous methylation patterns may be used for the downstream analyses as described below in Section IV.

In one embodiment, the analytics system uses 355 a sliding window to determine possibilities of methylation state vectors and calculate p-values. Rather than enumerating possibilities and calculating p-values for entire methylation state vectors, the analytics system enumerates possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window identifies the sequential set of CpG sites from the vector within the window starting from the first CpG site in the vector. The analytic system calculates a p-value score for the window including the first CpG site. The analytics system then "slides" the window to the second CpG site in the vector, and calculates another p-value score for the second window. Thus, for a window size l and methylation vector length m, each methylation state vector will generate m−l+1 p-value scores. After completing the p-value calculations for each portion of the vector, the lowest p-value score from all sliding windows is taken as the overall p-value score for the methylation state vector. In another embodiment, the analytics system aggregates the p-value scores for the methylation state vectors to generate an overall p-value score.

Using the sliding window helps to reduce the number of enumerated possibilities of methylation state vectors and their corresponding probability calculations that would otherwise need to be performed. To give a realistic example, it is possible for fragments to have upwards of 54 CpG sites. Instead of computing probabilities for $2^{54}$ (~$1.8 \times 10^{16}$) possibilities to generate a single p-score, the analytics system can instead use a window of size 5 (for example) which results in 50 p-value calculations for each of the 50 windows of the methylation state vector for that fragment. Each of the 50 calculations enumerates $2^5$ (32) possibilities of methylation state vectors, which total results in $50 \times 2^5$ ($1.6 \times 10^3$) probability calculations. This results in a vast reduction of calculations to be performed, with no meaningful hit to the accurate identification of anomalous fragments.

In embodiments with indeterminate states, the analytics system may calculate a p-value score summing out CpG sites with indeterminates states in a fragment's methylation state vector. The analytics system identifies all possibilities that have consensus with all methylation states of the methylation state vector excluding the indeterminate states. The analytics system may assign the probability to the methylation state vector as a sum of the probabilities of the identified possibilities. As an example, the analytics system calculates a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states uses calculations of probabilities of possibilities up to $2^i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In one embodiment, the computational burden of calculating probabilities and/or p-value scores may be further reduced by caching at least some calculations. For example, the analytics system may cache in transitory or persistent memory calculations of probabilities for possibilities of methylation state vectors (or windows thereof). If other fragments have the same CpG sites, caching the possibility probabilities allows for efficient calculation of p-score values without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

III.B. Hypermethylated Fragments and Hypomethylated Fragments

In another embodiment, the analytics system further defines anomalous fragments as fragments with over a threshold number of CpG sites and either with over a threshold percentage of the CpG sites methylated or with over a threshold percentage of CpG sites unmethylated; the analytics system identifies such fragments as hypermethylated fragments or hypomethylated fragments or more generally a UFXM. Example thresholds for length of fragments (or CpG sites) include more than 3, 4, 5, 6, 7, 8, 9, 10, etc. Example percentage thresholds of methylation or unmethylation include more than 80%, 85%, 90%, or 95%, or any other percentage within the range of 50%-100%.

IV. Cancer Classifier

IV.A. Training of Cancer Classifier

FIG. 4 is a flowchart describing a process 400 of training a cancer classifier, according to an embodiment. The analytics system obtains 410 a plurality of training samples each having a set of anomalous fragments and a label of cancer type. The anomalous fragments may be processed and identified according to the any combination of principles described in Sections II. and III., for example. The plurality of training samples includes any combination of samples from healthy individuals with a general label of "non-cancer," samples from subjects with a general label of "cancer" or a specific label (e.g., "breast cancer," "lung cancer," etc.). The training samples from subjects for one cancer type may be termed a cohort for that cancer type or a cancer type cohort.

The analytics system determines 420, for each training sample, a feature vector based on the set of anomalous fragments of the training sample. The analytics system calculates an anomaly score for each CpG site in an initial set of CpG sites. The initial set of CpG sites may be all CpG sites in the human genome or some portion thereof—which may be on the order of $10^4$, $10^5$, $10^6$, $10^7$, $10^8$, etc. In one embodiment, the analytics system defines the anomaly score for the feature vector with a binary scoring based on whether there is an anomalous fragment in the set of anomalous fragments that encompasses the CpG site. In another embodiment, the analytics system defines the anomaly score based on a count of anomalous fragments overlapping the CpG site. In one example, the analytics system may use a trinary scoring assigning a first score for lack of presence of anomalous fragments, a second score for presence of a few anomalous fragments (e.g., greater than zero but less than a threshold number of anomalous fragments), and a third score for presence of more than a few anomalous fragments (e.g., greater than the threshold number of anomalous fragments). For example, the analytics system counts 5 anomalous fragment in a sample that overlap the CpG site and calculates an anomaly score based on the count of 5.

Once all anomaly scores are determined for a training sample, the analytics system determines the feature vector as a vector of elements including, for each element, one of the anomaly scores associated with one of the CpG sites in an initial set. The analytics system normalizes the anomaly scores of the feature vector based on a coverage of the sample. Here, coverage refers to a median or average sequencing depth over all CpG sites covered by the initial set of CpG sites used in the classifier, or based on the set of anomalous fragments for a given training sample.

The analytics system may further limit the CpG sites considered for use in the cancer classifier. The analytics system computes 430, for each CpG site in the initial set of CpG sites, an information gain based on the feature vectors of the training samples. From step 420, each training sample has a feature vector that may contain an anomaly score all CpG sites in the initial set of CpG sites which could include up to all CpG sites in the human genome. However, some CpG sites in the initial set of CpG sites may not be as informative as others in distinguishing between cancer types, or may be duplicative with other CpG sites.

In one embodiment, the analytics system computes 430 an information gain for each cancer type and for each CpG site in the initial set to determine whether to include that CpG site in the classifier. The information gain is computed for training samples with a given cancer type compared to all other samples. For example, two random variables 'anomalous fragment' ('AF') and 'cancer type' ('CT') are used. In one embodiment, AF is a binary variable indicating whether there is an anomalous fragment overlapping a given CpG site in one or more given samples as determined for the anomaly score/feature vector above. CT is a random variable indicating whether the cancer is of a particular type. The analytics system computes the mutual information with respect to CT given AF. That is, how many bits of information about the cancer type are gained if it is known whether there is an anomalous fragment overlapping a particular CpG site.

For a given cancer type, the analytics system uses this information to rank CpG sites based on how cancer specific they are. This procedure is repeated for all cancer types under consideration. If a particular region is commonly anomalously methylated in training samples of a given cancer but not in training samples of other cancer types or in healthy training samples, then CpG sites overlapped by those anomalous fragments will tend to have high information gains for the given cancer type. The ranked CpG sites for each cancer type are greedily added (selected) 440 to a selected set of CpG sites based on their rank for use in the cancer classifier.

In additional embodiments, the analytics system may consider other selection criteria for selecting informative CpG sites to be used in the cancer classifier. One selection criterion may be that the selected CpG sites are above a threshold separation from other selected CpG sites. For example, the selected CpG sites are to be over a threshold number of base pairs away from any other selected CpG site (e.g., 100 base pairs), such that CpG sites that are within the threshold separation are not both selected for consideration in the cancer classifier.

In one embodiment, according to the selected set of CpG sites from the initial set, the analytics system may modify 450 the feature vectors of the training samples as needed. For example, the analytics system may truncate feature vectors to remove anomaly scores corresponding to CpG sites not in the selected set of CpG sites.

With the feature vectors of the training samples, the analytics system may train the cancer classifier in any of a number of ways. The feature vectors may correspond to the initial set of CpG sites from step 420 or to the selected set of CpG sites from step 450. In one embodiment, the analytics system trains 460 a binary cancer classifier to distinguish between a cancer classification and a non-cancer classification based on the feature vectors of the training samples. In this manner, the analytics system uses training samples that include both non-cancer samples from healthy individuals and cancer samples from individuals with cancer. Each training sample has one of the two labels "cancer" or "non-cancer." In this embodiment, the classifier outputs a cancer prediction indicating the likelihood of the presence or absence of cancer.

In another embodiment, the analytics system trains 450 a multiclass cancer classifier to distinguish between many cancer types. The possible set of cancer types may include one or more cancers and may also include a non-cancer type. Likewise, the set of cancer types may also include any additional other diseases or genetic disorders, etc. To do so, the analytics system uses the cancer type cohorts and may also include or not include a non-cancer type cohort. In this multi-cancer classifier embodiment, the cancer classifier is trained to determine a cancer prediction that comprises a prediction value for each of the cancer types being classified. The prediction values may correspond to a likelihood that a given training sample (and during inference, a test sample) has each of the cancer types.

In one implementation, the prediction values are scored between 0 and 100, wherein the cumulation of the prediction values equals 100. For example, the cancer classifier returns a cancer prediction including a prediction value for breast cancer, lung cancer, and non-cancer. In this example, the classifier can return a cancer prediction that a test sample is 65% likelihood of breast cancer, 25% likelihood of lung cancer, and 10% likelihood of non-cancer. The analytics system may further process the prediction values to generate a single cancer determination. Continuing with the example above and given the percentages, in this example the system may determine that the sample has breast cancer given that breast cancer has the highest likelihood. It should also be noted that the multi-cancer classifier can classify a test sample and produce a score for each of the types of cancer associated with the multi-cancer classifier such that the scores are independent of each other (and thus do not necessarily add up to 100). In this embodiment, the classifier may output a 90% likelihood of breast cancer and an 80% likelihood of lung cancer, indicating that the individual associated with the test sample has more than one type of cancer (or has a cancer that has metastasized to a different location).

In both embodiments, the analytics system trains the cancer classifier by inputting sets of training samples with their feature vectors into the cancer classifier and adjusting classification parameters so that a function of the classifier accurately relates the training feature vectors to their corresponding label. The analytics system may group the training samples into sets of one or more training samples for iterative batch training of the cancer classifier. After inputting all sets of training samples including their training feature vectors and adjusting the classification parameters, the cancer classifier is sufficiently trained to label test samples according to their feature vector within some margin of error. The analytics system may train the cancer classifier according to any one of a number of methods. As an example, the binary cancer classifier may be a L2-regularized logistic regression classifier that is trained using a log-loss function. As other examples, the multi-cancer classifier may be a multinomial logistic regression or a non-linear regression. In practice either type of cancer classifier may be trained using other techniques. These techniques are numerous including potential use of kernel methods, random forest classifier, a mixture model, an autoencoder model, machine learning algorithms such as multilayer neural networks, etc.

IV.B. Deployment of the Cancer Classifier

During use of the cancer classifier, the analytics system obtains a test sample from a subject of unknown cancer type. The analytics system may process the test sample comprised of DNA molecules with any combination of the processes described in Sections II. and III. to achieve a set of anomalous fragments. The analytics system determines a test feature vector for use by the cancer classifier according to similar principles discussed in the process 400. The analytics system calculates an anomaly score for each CpG site in a plurality of CpG sites in use by the cancer classifier. For example, the cancer classifier receives as input feature vectors inclusive of anomaly scores for 1,000 selected CpG sites. The analytics system thus determines a test feature vector inclusive of anomaly scores for the 1,000 selected CpG sites based on the set of anomalous fragments. The analytics system calculates the anomaly scores in a same manner as the training samples. In one embodiment, the analytics system defines the anomaly score as a binary score based on whether there is a hypermethylated or hypomethylated fragment in the set of anomalous fragments that encompasses the CpG site.

The analytics system then inputs the test feature vector into the cancer classifier. The cancer classifier, when applied to the test feature vector, generates a cancer prediction based on the classification parameters trained in the process 400 and the test feature vector. In the first manner, the cancer prediction is binary and selected from a group consisting of "cancer" or non-cancer;" in the second manner, the cancer prediction is selected from a group of many cancer types and "non-cancer." In additional embodiments, the cancer prediction has predictions values for each of the many cancer types. Moreover, the analytics system may determine that the test sample is most likely to be of one of the cancer types. Following the example above with the cancer prediction for a test sample as 65% likelihood of breast cancer, 25% likelihood of lung cancer, and 10% likelihood of non-cancer, the analytics system may determine that the test sample is most likely to have breast cancer. In another example, where the cancer prediction is binary as 60% likelihood of non-cancer and 40% likelihood of cancer, the analytics system determines that the test sample is most likely not to have cancer. In additional embodiments, the cancer type prediction with the highest likelihood may still be compared against a threshold (e.g., 40%, 50%, 60%, 70%) in order to classify the test subject as having that cancer type. If the cancer prediction with the highest likelihood does not surpass that threshold, the analytics system may return an inconclusive result.

In additional embodiments, the analytics system chains a cancer classifier trained in step 460 of the process 400 with another cancer classifier trained in step 470 or the process 400. The analytics system inputs the test feature vector into the cancer classifier trained as a binary classifier in step 460 of the process 400. The analytics system receives an output of a cancer prediction. The cancer prediction may be binary, indicating whether the test subject likely has or likely does not have cancer. In other implementations, the cancer prediction includes prediction values that describe likelihood of cancer and likelihood of non-cancer. For example, the cancer prediction has a cancer prediction value of 85% and the non-cancer prediction value of 15%. The analytics system may determine the test subject to likely have cancer. Once the analytics system determines a test subject is likely to have cancer, the analytics system may input the test feature vector into a multiclass cancer classifier trained to distinguish between different cancer types. The multiclass cancer classifier receives the test feature vector and returns a cancer prediction of a cancer type of the plurality of cancer types. For example, the multiclass cancer classifier provides a cancer prediction specifying that the test subject is most likely to have ovarian cancer. In another implementation, the multiclass cancer classifier provides a prediction value for each cancer type of the plurality of cancer types. For example, a cancer prediction may include a breast cancer type prediction value of 40%, a colorectal cancer type prediction value of 15%, and a liver cancer prediction value of 45%.

In some embodiments, in response to the cancer classifier outputting a cancer prediction for a test sample (e.g., either the likelihood of the presence or absence of cancer generally, or the likelihood of the presence or absence of a particular type of cancer), the prediction can be clinically verified. For instance, an individual predicted to have lung cancer can be diagnosed as having lung cancer or not having lung cancer by a physician, or an individual predicted to be cancer-free can be diagnosed with cancer by a physician. In response to the verification or contradiction of the cancer prediction outputted by the cancer classifier, the feature vector associated with the test sample can be added to the training sample set with a label representative of the verification or contradiction (e.g., the feature vector can be labeled "lung cancer," "non-cancer", and the like). The classifier can then be retrained using the updated training sample set in order to improve the performance of the classifier in subsequent applications.

V. Applications

In some embodiments, the methods, analytic systems and/or classifier of the present invention can be used to detect the presence of cancer, monitor cancer progression or recurrence, monitor therapeutic response or effectiveness, determine a presence or monitor minimum residual disease (MRD), or any combination thereof. For example, as described herein, a classifier can be used to generate a probability score (e.g., from 0 to 100) describing a likelihood that a test feature vector is from a subject with cancer. In some embodiments, the probability score is compared to a threshold probability to determine whether or not the subject has cancer. In other embodiments, the likelihood or probability score can be assessed at multiple different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the probability score exceeds a threshold, a physician can prescribe an appropriate treatment.

V.A. Early Detection of Cancer

In some embodiments, the methods and/or classifier of the present invention are used to detect the presence or absence of cancer in a subject suspected of having cancer. For example, a classifier (e.g., as described above in Section IV) can be used to determine a cancer prediction describing a likelihood that a test feature vector is from a subject that has cancer.

In one embodiment, a cancer prediction is a likelihood (e.g., scored between 0 and 100) for whether the test sample has cancer (i.e. binary classification). Thus, the analytics system may determine a threshold for determining whether a test subject has cancer. For example, a cancer prediction of greater than or equal to 60 can indicate that the subject has cancer. In still other embodiments, a cancer prediction greater than or equal to 65, greater than or equal to 70, greater than or equal to 75, greater than or equal to 80, greater than or equal to 85, greater than or equal to 90, or greater than or equal to 95 indicates that the subject has cancer. In other embodiments, the cancer prediction can indicate the severity of disease. For example, a cancer prediction of 80 may indicate a more severe form, or later stage, of cancer compared to a cancer prediction below 80 (e.g., a probability score of 70). Similarly, an increase in the cancer prediction over time (e.g., determined by classifying test feature vectors from multiple samples from the same subject taken at two or more time points) can indicate disease progression or a decrease in the cancer prediction over time can indicate successful treatment.

In another embodiment, a cancer prediction comprises many prediction values, wherein each of a plurality of cancer types being classified (i.e. multiclass classification) for has a prediction value (e.g., scored between 0 and 100). The prediction values may correspond to a likelihood that a given training sample (and during inference, training sample) has each of the cancer types. The analytics system may identify the cancer type that has the highest prediction value and indicate that the test subject likely has that cancer type. In other embodiments, the analytics system further compares the highest prediction value to a threshold value (e.g., 50, 55, 60, 65, 70, 75, 80, 85, etc.) to determine that the test subject likely has that cancer type. In other embodiments, a prediction value can also indicate the severity of disease. For example, a prediction value greater than 80 may indicate a more severe form, or later stage, of cancer compared to a prediction value of 60. Similarly, an increase in the prediction value over time (e.g., determined by classifying test feature vectors from multiple samples from the same subject taken at two or more time points) can indicate disease progression or a decrease in the prediction value over time can indicate successful treatment.

According to aspects of the invention, the methods and systems of the present invention can be trained to detect or classify multiple cancer indications. For example, the methods, systems and classifiers of the present invention can be used to detect the presence of one or more, two or more, three or more, five or more, ten or more, fifteen or more, or twenty or more different types of cancer.

Examples of cancers that can be detected using the methods, systems and classifiers of the present invention include carcinoma, lymphoma, blastoma, sarcoma, and leukemia or lymphoid malignancies. More particular examples of such cancers include, but are not limited to, squamous cell cancer (e.g., epithelial squamous cell cancer), skin carcinoma, melanoma, lung cancer, including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer (e.g., pancreatic ductal adenocarcinoma), cervical cancer, ovarian cancer (e.g., high grade serous ovarian carcinoma), liver cancer (e.g., hepatocellular carcinoma (HCC)), hepatoma, hepatic carcinoma, bladder cancer (e.g., urothelial bladder cancer), testicular (germ cell tumor) cancer, breast cancer (e.g., HER2 positive, HER2 negative, and triple negative breast cancer), brain cancer (e.g., astrocytoma, glioma (e.g., glioblastoma)), colon cancer, rectal cancer, colorectal cancer, endometrial or uterine carcinoma, salivary gland carcinoma, kidney or renal cancer (e.g., renal cell carcinoma, nephroblastoma or Wilms' tumor), prostate cancer, vulval cancer, thyroid cancer, anal carcinoma, penile carcinoma, head and neck cancer, esophageal carcinoma, and nasopharyngeal carcinoma (NPC). Additional examples of cancers include, without limitation, retinoblastoma, thecoma, arrhenoblastoma, hematologic malignancies, including but not limited to non-Hodgkin's lymphoma (NHL), multiple myeloma and acute hematologic malignancies, endometriosis, fibrosarcoma, choriocarcinoma, laryngeal carcinomas, Kaposi's sarcoma, Schwannoma, oligodendroglioma, neuroblastomas, rhabdomyosarcoma, osteogenic sarcoma, leiomyosarcoma, and urinary tract carcinomas.

In some embodiments, the cancer is one or more of anorectal cancer, bladder cancer, breast cancer, cervical cancer, colorectal cancer, esophageal cancer, gastric cancer, head & neck cancer, hepatobiliary cancer, leukemia, lung cancer, lymphoma, melanoma, multiple myeloma, ovarian cancer, pancreatic cancer, prostate cancer, renal cancer, thyroid cancer, uterine cancer, or any combination thereof.

In some embodiments, the one or more cancer can be a "high-signal" cancer (defined as cancers with greater than 50% 5-year cancer-specific mortality), such as anorectal, colorectal, esophageal, head & neck, hepatobiliary, lung, ovarian, and pancreatic cancers, as well as lymphoma and multiple myeloma. High-signal cancers tend to be more aggressive and typically have an above-average cell-free nucleic acid concentration in test samples obtained from a patient.

V.B. Cancer and Treatment Monitoring

In some embodiments, the cancer prediction can be assessed at multiple different time points (e.g., or before or after treatment) to monitor disease progression or to monitor treatment effectiveness (e.g., therapeutic efficacy). For example, the present invention include methods that involve obtaining a first sample (e.g., a first plasma cfDNA sample) from a cancer patient at a first time point, determining a first cancer prediction therefrom (as described herein), obtaining a second test sample (e.g., a second plasma cfDNA sample) from the cancer patient at a second time point, and determining a second cancer prediction therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the classifier is utilized to monitor the effectiveness of the treatment. For example, if the second cancer prediction decreases compared to the first cancer prediction, then the treatment is considered to have been successful. However, if the second cancer prediction increases compared to the first cancer prediction, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., after a resection surgery or a therapeutic intervention). In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

Those of skill in the art will readily appreciate that test samples can be obtained from a cancer patient over any desired set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 30 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 3 months, at least once every 6 months, at least once a year, at least once every 2 years, at least once every 3 years, at least once every 4 years, or at least once every 5 years.

V.C. Treatment

In still another embodiment, the cancer prediction can be used to make or influence a clinical decision (e.g., diagnosis of cancer, treatment selection, assessment of treatment effectiveness, etc.). For example, in one embodiment, if the cancer prediction (e.g., for cancer or for a particular cancer type) exceeds a threshold, a physician can prescribe an appropriate treatment (e.g., a resection surgery, radiation therapy, chemotherapy, and/or immunotherapy).

A classifier (as described herein) can be used to determine a cancer prediction that a sample feature vector is from a subject that has cancer. In one embodiment, an appropriate treatment (e.g., resection surgery or therapeutic) is prescribed when the cancer prediction exceeds a threshold. For example, in one embodiment, if the cancer prediction is greater than or equal to 60 one or more appropriate treatments are prescribed. In another embodiments, if the cancer prediction is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, the cancer prediction can indicate the severity of disease. An appropriate treatment matching the severity of the disease may then be prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

VI. Example Sequencer and Analytics System

Figure 5A:
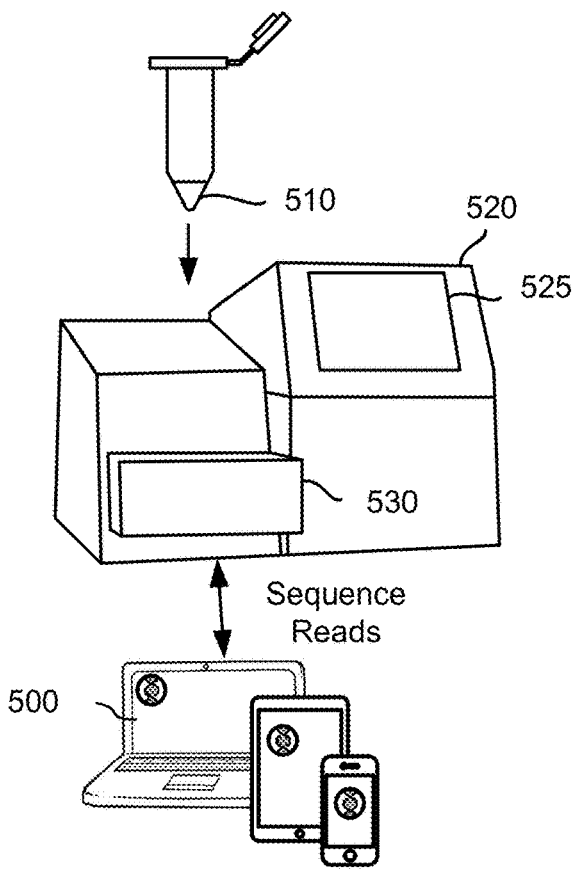
FIG. 5A illustrates a flowchart of devices for sequencing nucleic acid samples according to one embodiment.

FIG. 5A is a flowchart of devices for sequencing nucleic acid samples according to one embodiment. This illustrative flowchart includes devices such as a sequencer 520 and an analytics system 500. The sequencer 520 and the analytics system 500 may work in tandem to perform one or more steps in the processes 100 of FIG. 1A, 200 of FIG. 2A, 300 and 320 of FIG. 3, 400 of FIG. 4, and other process described herein.

In various embodiments, the sequencer 520 receives an enriched nucleic acid sample 510. As shown in FIG. 5A, the sequencer 520 can include a graphical user interface 525 that enables user interactions with particular tasks (e.g., initiate sequencing or terminate sequencing) as well as one more loading stations 530 for loading a sequencing cartridge including the enriched fragment samples and/or for loading necessary buffers for performing the sequencing assays. Therefore, once a user of the sequencer 520 has provided the necessary reagents and sequencing cartridge to the loading station 530 of the sequencer 520, the user can initiate sequencing by interacting with the graphical user interface 525 of the sequencer 520. Once initiated, the sequencer 520 performs the sequencing and outputs the sequence reads of the enriched fragments from the nucleic acid sample 510.

In some embodiments, the sequencer 520 is communicatively coupled with the analytics system 500. The analytics system 500 includes some number of computing devices used for processing the sequence reads for various applications such as assessing methylation status at one or more CpG sites, variant calling or quality control. The sequencer 520 may provide the sequence reads in a BAM file format to the analytics system 500. The analytics system 500 can be communicatively coupled to the sequencer 520 through a wireless, wired, or a combination of wireless and wired communication technologies. Generally, the analytics system 500 is configured with a processor and non-transitory computer-readable storage medium storing computer instructions that, when executed by the processor, cause the processor to process the sequence reads or to perform one or more steps of any of the methods or processes disclosed herein this disclosure.

In some embodiments, the sequence reads may be aligned to a reference genome using known methods in the art to determine alignment position information, e.g., part of step 140 of the process 100 in FIG. 1A. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 500 may label a sequence read with one or more genes that align to the sequence read. In one embodiment, fragment length (or size) is be determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome represent the likely location within the reference genome to which the nucleic acid fragment corresponds. An output file having SAM (sequence alignment map) format or BAM (binary) format may be generated and output for further analysis.

Figure 5B:
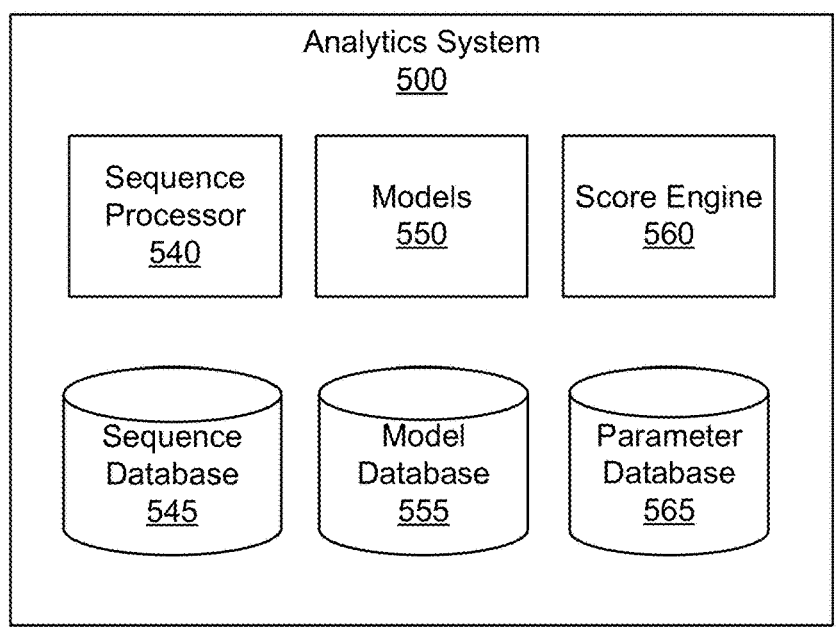
FIG. 5B is a block diagram of an analytics system, according to an embodiment.

Referring now to FIG. 5B, FIG. 5B is a block diagram of an analytics system 500 for processing DNA samples according to one embodiment. The analytics system implements one or more computing devices for use in analyzing DNA samples. The analytics system 500 includes a sequence processor 540, sequence database 545, model database 555, models 550, parameter database 565, and score engine 560. In some embodiments, the analytics system 500 performs one or more steps in the processes 100 of FIG. 1A, 200 of FIG. 2A, 300 and 320 of FIG. 3, 400 of FIG. 4, and other process described herein.

The sequence processor 540 generates methylation state vectors for fragments from a sample. At each CpG site on a fragment, the sequence processor 540 generates a methylation state vector for each fragment specifying a location of the fragment in the reference genome, a number of CpG sites in the fragment, and the methylation state of each CpG site in the fragment whether methylated, unmethylated, or indeterminate via the process 100 of FIG. 1A. The sequence processor 540 may store methylation state vectors for fragments in the sequence database 545. Data in the sequence database 545 may be organized such that the methylation state vectors from a sample are associated to one another.

Further, multiple different models 550 may be stored in the model database 555 or retrieved for use with test samples. In one example, a model is a trained cancer classifier for determining a cancer prediction for a test sample using a feature vector derived from anomalous fragments. The training and use of the cancer classifier discussed above in conjunction with Section IV. Cancer Classifier. The analytics system 500 may train the one or more models 550 and store various trained parameters in the parameter database 565. The analytics system 500 stores the models 550 along with functions in the model database 555.

During inference, the score engine 560 uses the one or more models 550 to return outputs. The score engine 560 accesses the models 550 in the model database 555 along with trained parameters from the parameter database 565. According to each model, the score engine receives an appropriate input for the model and calculates an output based on the received input, the parameters, and a function of each model relating the input and the output. In some use cases, the score engine 560 further calculates metrics correlating to a confidence in the calculated outputs from the model. In other use cases, the score engine 560 calculates other intermediary values for use in the model.

VII. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, thereby providing a framework for various possibilities of described embodiments to function together.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for identifying duplicate deoxyribonucleic acid (DNA) fragments from a test subject and identifying a cancer presence in the test subject, the method comprising:
   sequencing a physical sample obtained from the test subject, the sequenced sample comprising a plurality of fragments, wherein the plurality of fragments comprises at least one duplicate DNA fragment;
   identifying a first fragment and a second fragment of the plurality of fragments from the sample as being derived from a matching reference location;
   generating a first methylation state vector for the first fragment and a second methylation state vector for the second fragment, each methylation state vector comprising a methylation state for each of a set of CpG sites, each methylation state comprising one of: methylated, unmethylated, variant, and ambiguous;
   for each CpG site of the set of CpG sites, computing a difference score for the CpG site based on whether the methylation state at the CpG site included in the first methylation state vector agrees or disagrees with the methylation state at the CpG site included in the second methylation state vector;
   computing a modified Hamming distance based on the computed difference scores;
   in response to the modified Hamming distance not exceeding a threshold score, labeling the second fragment as a duplicate of the first fragment;
   generating a reduced set of fragments by removing the second fragment from the plurality of fragments based on its label as the duplicate of the first fragment; and
   applying a cancer prediction model to the reduced set of fragments to generate a cancer prediction for the test subject.

2. The method of claim 1, wherein the first fragment comprises a first pair of sequence reads and the second fragment comprises a second pair of sequence reads, and wherein computing a difference score for a CpG site is based further on whether one or both methylation states at the CpG site within the first pair of sequence reads disagrees with one or both methylation states at the CpG site within the second pair of sequence reads.

3. The method of claim 2, wherein a first difference score is greater than a second difference score, the first difference score for a first CpG site with both methylation states within the first pair of sequence reads comprising a methylated state and at least one methylation states within the second pair of sequence reads comprising an unmethylated state, and the second difference score for a second CpG site in which only one methylation states within the first pair of sequence reads comprises a methylated state and only one methylation state within the second pair of sequence reads comprises an unmethylated state.

4. The method of claim 1, wherein a difference score for a CpG site with a methylation state of methylated or unmethylated within the first methylation state vector is the same for:
a matching methylation state within the second methylation state vector,
a methylation state of variant within the second methylation state vector, and
a methylation state of ambiguous within the second methylation state vector.

5. The method of claim 1, wherein a first difference score is less than a second difference score, the first difference score for a first CpG site with a methylation state of methylated within the first methylation state vector and the second methylation state vector, and the second difference score for a second CpG site with a methylation state of methylated within the first methylation state vector and a methylation state of unmethylated within the second methylation state vector.

6. The method of claim 1, wherein computing the modified Hamming distance comprises summing the computed difference scores for each CpG site in the set of CpG sites.

7. The method of claim 1, wherein the first fragment and the second fragment are identified as being derived from the matching reference location if the first fragment and the second fragment have matching start reference locations and matching end reference locations.

8. The method of claim 1, further comprising:
identifying a set of unique fragments from the plurality of fragments, each of the unique fragments in the set having a modified Hamming distance exceeding the threshold score when compared against other fragments having a matching reference location; and
applying a cancer prediction model to the set of unique fragments to generate a cancer prediction for the test subject, the cancer prediction model configured to produce a likelihood of cancer for the test subject for each of one or more cancer types based at least in part on the methylation states of the unique fragments.

9. The method of claim 8, further comprising:
filtering the set of unique fragments with p-value filtering to generate a set of anomalous fragments, the filtering comprising removing fragments from the set of unique fragments having below a threshold p-value with respect to others to produce the set of anomalous fragments,
wherein the cancer prediction model is applied to the set of anomalous fragments to generate the cancer prediction for the test subject.

10. The method of claim 9, wherein each anomalous fragment is also hypomethylated or hypermethylated such that the anomalous fragment includes at least a threshold number of CpG sites with more than a threshold percentage of the CpG sites being unmethylated or with more than the threshold percentage of the CpG sites being methylated, respectively.

11. The method of claim 9, wherein applying a cancer prediction model to the set of anomalous fragments to generate the cancer prediction for the test subject comprises:
generating a test feature vector by generating for each of a plurality of CpG sites from a reference genome a score based on whether one or more of the anomalous fragments overlaps the CpG site;
inputting the test feature vector into the cancer prediction model to generate the cancer prediction for the test subject comprising a plurality of cancer prediction values, each cancer prediction value describing a likelihood the test sample is of a particular cancer type of the one or more cancer types, the cancer prediction model comprising:
a plurality of classification parameters, and
a function representing a relation between the test feature vector received as input and the cancer prediction generated as output based on the test feature vector and the plurality of classification parameters; and
determining whether or not the test subject has a first cancer type from the one or more cancer types based on the cancer prediction.

12. The method of claim 11, wherein the cancer prediction model is a neural network having a plurality of layers including an input layer for receiving the test feature vector and an output layer for returning the cancer prediction based on the test feature vector, wherein the function and the plurality of classification parameters define edges between nodes of the plurality of layers.

13. The method of claim 11, wherein the function is one of:
a logistic regression;
a multinomial regression; and
a non-linear regression.

14. A non-transitory computer-readable storage medium for identifying duplicate deoxyribonucleic acid (DNA) fragments from a test subject and identifying a cancer presence in the test subject, the storage medium storing encoded instructions that, when executed by a processor, cause the processor to perform operations comprising:
sequencing a physical sample obtained from the test subject, the sequenced sample comprising a plurality of fragments, wherein the plurality of fragments comprises at least one duplicate DNA fragment;
identifying a first fragment and a second fragment of the plurality of fragments from the sample as being derived from a matching reference location;
generating a first methylation state vector for the first fragment and a second methylation state vector for the second fragment, each methylation state vector comprising a methylation state for each of a set of CpG sites, each methylation state comprising one of: methylated, unmethylated, variant, and ambiguous;
for each CpG site of the set of CpG sites, computing a difference score for the CpG site based on whether the methylation state at the CpG site included in the first methylation state vector agrees or disagrees with the methylation state at the CpG site included in the second methylation state vector;
computing a modified Hamming distance based on the computed difference scores;
in response to the modified Hamming distance not exceeding a threshold score, labeling the second fragment as a duplicate of the first fragment;
generating a reduced set of fragments by removing the second fragment from the plurality of fragments based on its label as the duplicate of the first fragment; and
applying a cancer prediction model to the reduced set of fragments to generate a cancer prediction for the test subject.

15. The storage medium of claim 14, wherein the first fragment comprises a first pair of sequence reads and the second fragment comprises a second pair of sequence reads, and wherein computing a difference score for a CpG site is based further on whether one or both methylation states at the CpG site within the first pair of sequence reads disagrees with one or both methylation states at the CpG site within the second pair of sequence reads.

16. The storage medium of claim 15, wherein a first difference score is greater than a second difference score, the first difference score for a first CpG site with both methylation states within the first pair of sequence reads comprising a methylated state and at least one methylation states within the second pair of sequence reads comprising an unmethylated state, and the second difference score for a second CpG site in which only one methylation states within the first pair of sequence reads comprises a methylated state and only one methylation state within the second pair of sequence reads comprises an unmethylated state.

17. The storage medium of claim 14, wherein a first difference score is less than a second difference score, the first difference score for a first CpG site with a methylation state of methylated within the first methylation state vector and the second methylation state vector, and the second difference score for a second CpG site with a methylation state of methylated within the first methylation state vector and a methylation state of unmethylated within the second methylation state vector.

18. The storage medium of claim 14, wherein computing the modified Hamming distance comprises summing the computed difference scores for each CpG site in the set of CpG sites.

19. The storage medium of claim 14, wherein the first fragment and the second fragment are identified as being derived from the matching reference location if the first fragment and the second fragment have matching start reference locations and matching end reference locations.

20. The storage medium of claim 14, further comprising:
 identifying a set of unique fragments from the plurality of fragments, each of the unique fragments in the set having a modified Hamming distance exceeding the threshold score when compared against other fragments having a matching reference location; and
 applying a cancer prediction model to the set of unique fragments to generate a cancer prediction for the test subject, the cancer prediction model configured to produce a likelihood of cancer for the test subject for each of one or more cancer types based at least in part on the methylation states of the unique fragments.

21. A system for identifying duplicate fragments of deoxyribonucleic acid (DNA) from a test subject and identifying a cancer presence in the test subject, the system comprising:
 a processor; and
 a non-transitory computer-readable storage medium storing encoded instructions that, when executed by a processor, cause the processor to perform operations comprising:
  sequencing a physical sample obtained from the test subject, the sequenced sample comprising a plurality of fragments, wherein the plurality of fragments comprises at least one duplicate DNA fragment;
  identifying a first fragment and a second fragment of the plurality of fragments from the sample as being derived from a matching reference location;
  generating a first methylation state vector for the first fragment and a second methylation state vector for the second fragment, each methylation state vector comprising a methylation state for each of a set of CpG sites, each methylation state comprising one of: methylated, unmethylated, variant, and ambiguous;
  for each CpG site of the set of CpG sites, computing a difference score for the CpG site based on whether the methylation state at the CpG site included in the first methylation state vector agrees or disagrees with the methylation state at the CpG site included in the second methylation state vector;
  computing a modified Hamming distance based on the computed difference scores;
  in response to the modified Hamming distance not exceeding a threshold score, labeling the second fragment as a duplicate of the first fragment;
  generating a reduced set of fragments by removing the second fragment from the plurality of fragments based on its label as the duplicate of the first fragment; and
  applying a cancer prediction model to the reduced set of fragments to generate a cancer prediction for the test subject.

* * * * *